US008367406B2

(12) United States Patent
Kopyov

(10) Patent No.: US 8,367,406 B2
(45) Date of Patent: *Feb. 5, 2013

(54) PLURIPOTENT CELLS

(75) Inventor: Oleg V. Kopyov, Moorpark, CA (US)

(73) Assignee: Celavie Biosciences, LLC, Reading, PA (US)

( * ) Notice: Subject to any disclaimer, the term of this patent is extended or adjusted under 35 U.S.C. 154(b) by 67 days.

This patent is subject to a terminal disclaimer.

(21) Appl. No.: 12/506,128

(22) Filed: Jul. 20, 2009

(65) Prior Publication Data
US 2009/0280097 A1 Nov. 12, 2009

Related U.S. Application Data

(60) Division of application No. 11/755,224, filed on May 30, 2007, now abandoned, and a continuation-in-part of application No. 11/002,933, filed on Dec. 2, 2004, now Pat. No. 7,632,681.

(60) Provisional application No. 60/803,619, filed on May 31, 2006, provisional application No. 60/526,242, filed on Dec. 2, 2003.

(51) Int. Cl.
C12N 5/00 (2006.01)
C12N 5/02 (2006.01)
C12N 5/07 (2010.01)
C12N 5/10 (2006.01)
C12N 5/071 (2010.01)

(52) U.S. Cl. ........ 435/325; 435/352; 435/354; 435/363; 435/366; 435/383; 435/384; 435/404; 435/405

(58) Field of Classification Search .................. None
See application file for complete search history.

(56) References Cited

U.S. PATENT DOCUMENTS

| 5,750,376 | A | 5/1998 | Weiss et al. |
| 5,753,506 | A | 5/1998 | Johe |
| 5,843,780 | A | 12/1998 | Thomson |
| 5,851,832 | A | 12/1998 | Weiss et al. |
| 5,958,767 | A | 9/1999 | Snyder et al. |
| 5,968,829 | A | 10/1999 | Carpenter |
| 5,980,885 | A | 11/1999 | Weiss et al. |
| 5,981,165 | A | 11/1999 | Weiss et al. |
| 5,994,617 | A | 11/1999 | Dick et al. |
| 6,040,180 | A | 3/2000 | Johe |
| 6,071,889 | A | 6/2000 | Weiss et al. |
| 6,200,806 | B1 | 3/2001 | Thomson |
| 6,238,922 | B1 | 5/2001 | Uchida |
| 6,280,718 | B1 | 8/2001 | Kaufman et al. |
| 6,294,346 | B1 | 9/2001 | Weiss et al. |
| 6,395,546 | B1 | 5/2002 | Zobel et al. |
| 6,399,369 | B1 | 6/2002 | Weiss et al. |
| 6,468,794 | B1 | 10/2002 | Uchida et al. |
| 6,497,872 | B1 | 12/2002 | Weiss et al. |
| 6,498,018 | B1 | 12/2002 | Carpenter |
| 6,544,787 | B1 | 4/2003 | Slavin |
| 6,589,759 | B1 | 7/2003 | Loscalzo et al. |
| 6,602,711 | B1 | 8/2003 | Thomson et al. |
| 6,605,275 | B1 | 8/2003 | Boyse et al. |
| 6,610,535 | B1 | 8/2003 | Lu et al. |
| 6,613,568 | B2 | 9/2003 | Kaufman et al. |
| 6,749,850 | B1 | 6/2004 | Finkelstein et al. |
| 6,812,027 | B2 | 11/2004 | Goldman |
| 6,821,779 | B1 | 11/2004 | Koopmans et al. |
| 6,833,269 | B2 | 12/2004 | Carpenter |
| 7,132,286 | B2 | 11/2006 | Laeng et al. |
| 7,311,905 | B2 | 12/2007 | Hariri |
| 7,468,277 | B2 | 12/2008 | Goldman et al. |
| 7,504,100 | B2 | 3/2009 | Yu et al. |
| 7,517,521 | B2 | 4/2009 | Mayer-Proschel et al. |
| 7,547,522 | B2 | 6/2009 | Hawley |
| 7,632,681 | B2 * | 12/2009 | Kopyov ..................... 435/404 |
| 2001/0024825 | A1 | 9/2001 | Thomson |
| 2001/0038836 | A1 | 11/2001 | During et al. |
| 2002/0155096 | A1 | 10/2002 | Chancellor et al. |
| 2002/0178460 | A1 | 11/2002 | Enikolopov et al. |
| 2003/0008392 | A1 | 1/2003 | Thomson |
| 2003/0013193 | A1 | 1/2003 | Wu |
| 2003/0068819 | A1 | 4/2003 | Zhang et al. |
| 2003/0073234 | A1 | 4/2003 | Amit et al. |
| 2003/0100107 | A1 | 5/2003 | Peschle |
| 2003/0148512 | A1 | 8/2003 | Fanslow, III et al. |
| 2003/0166276 | A1 | 9/2003 | Carpenter |
| 2003/0190748 | A1 | 10/2003 | Thomson |
| 2003/0203844 | A1 | 10/2003 | Delfani et al. |
| 2003/0228295 | A1 | 12/2003 | Svendsen |
| 2004/0005701 | A1 | 1/2004 | Xu et al. |
| 2004/0023376 | A1 | 2/2004 | Thomson et al. |
| 2004/0224401 | A1 | 11/2004 | Ludwig et al. |
| 2005/0074880 | A1 | 4/2005 | Sang et al. |
| 2007/0014773 | A1 | 1/2007 | Matheny et al. |

(Continued)

FOREIGN PATENT DOCUMENTS
WO    WO 94/10292    5/1994

OTHER PUBLICATIONS

Calof, AL, and DM Chikaraishi, "Analysis of Neurogenesis in a Mammalian Neuroepithelium: Proliferation and Differentiation of an Olfactory Neuron Precursor In Vitro" *Neuron* 3:115-127, Jul. 1989.

Santa-Olalla, J, and L Covarrubias, "Epidermal Growth Factor (EGF), Transforming Growth Factor-$\alpha$ (TGF-$\alpha$), and Basic Fibroblast Growth Factor (bFGF) Differentially Influence Neural Precursor Cells of Mouse Embryonic Mesencephalon" *J. Neurosci. Res.* 42:172-183, 1995.

Galmés, A, et al. "Long-Term Storage at -80° C. of Hematopoetic Progenitor Cells With 5-Percent Dimethyl Sulfoxide as the Sole Cryoprotectant" *Transfusion* 39:70-73.

Trumble, TE, and JT Whalen, "The Effects of Cryosurgery and Cryoprotectants on Peripheral Nerve Function" *J. Reconstr. Microsurg.* 8:53-60, 1992.

(Continued)

Primary Examiner — Anne-Marie Falk
(74) Attorney, Agent, or Firm — Karen S. Canady; canady + lortz LLP

(57) ABSTRACT

Pluripotent cells that are immunopositive for both the neural progenitor marker nestin and a pluripotent cell marker are provided. The cells exhibit rapid doubling times and can be maintained in vitro for extended periods. Also provided are cell cultures containing the pluripotent cells, a method of transplanting human pluripotent cells to a host, and a method of reducing seizure activity in a subject. These pluripotent cells, when transplanted into the ventricle of a host animal, migrate to the site of damage and adopt a suitably corrective phenotype, resulting in both structural and functional restoration.

23 Claims, 21 Drawing Sheets

U.S. PATENT DOCUMENTS

| | | |
|---|---|---|
| 2007/0026520 A1 | 2/2007 | Kelly |
| 2007/0116684 A1 | 5/2007 | Atala et al. |
| 2007/0266448 A1 | 11/2007 | Lifke et al. |
| 2008/0213276 A1 | 9/2008 | Lindquist et al. |
| 2008/0233088 A1 | 9/2008 | Guha et al. |
| 2008/0318316 A1 | 12/2008 | Reid et al. |
| 2009/0022694 A1 | 1/2009 | Distefano |
| 2009/0022696 A1 | 1/2009 | Bernstein et al. |
| 2009/0214484 A1 | 8/2009 | Mironov |
| 2009/0298045 A1 | 12/2009 | Treves et al. |
| 2009/0324609 A1 | 12/2009 | Lodie et al. |
| 2010/0003754 A1 | 1/2010 | Briest et al. |

OTHER PUBLICATIONS

Balk, S.D. et al., "Roles of Calcium, Serum, Plasma, and Folic Acid in the Control of Proliferation of Normal and Rous Sarcoma Virus-Infected Chicken Fibroblasts", *Proc. Nat. Acad.Sci. USA*, Mar. 1973, 70(3):675-679.

Benniger, Yves et al., "Differentiation and Histological Analysis of Embryonic Stem Cell-derived Neural Transplants in Mice", *Brain Pathology*, 10: 330-341, 2001.

Bjornson, Christopher R. R. et al., "Turning Brain into Blood: A Hematopoietic Fate Adopted by Adult Neural Stem Cells in Vivo", *Science*, 283: 534-537, Jan. 22, 1999.

Carpenter, M.K., "Enrichment of Neurons and Neural Precursors from Human Embryonic Stem Cells", *Exp Neurol*, 172(2):383-97, Dec. 2001, (1-Page Abstract Only).

Craig, Constance G. et al., "In Vivo Growth Factor Expansion of Endogenous Subependymal Neural Precursor Cells Populations in the Adult Mouse Brain", *The Journal of Neuroscience*, 16(8):2649-2658, Apr. 15, 1996.

Eslamboli, A. Marmoset Monkey Models of Parkinson's Disease: Which Model, When and Why?, Brain Res Bull, Dec. 30, 2005, 68(3): 140-9. Epub Sep. 7, 2005.

Friker, Rosemary A. et al., "Site-Specific Migration and Neuronal Differentiation of Human Neural Progenitor Cells after Transplantation in the Adult Rat Brain", *The Journal of Neuroscience*, 19(14):5990-6005, Jul. 15, 1999.

Gaiano, Nicholas et al., "Transplantation as a Tool to Study Progenitors within the Vertebrate Nervous System", The Skirball Institute of Biomolecular Medicine, Developmental Genetics Program, NYU Medical Center, New York, © 1998 John Wiley & Sons, Inc., pp. 152-160.

Gerlach, M. et al., "Current State of Stem Cell Research for the Treatment of Parkinson's Disease", J Neurol. Oct. 2002, 249 Suppl 3:III/33-III-35.

Gritti, Angela et al., "Multipotential Stem Cells from the Adult Mouse Brain Proliferate and Self-Renew in Response to Basic Fibroblast Growth Factor", *The Journal of Neuroscience*, 16(3):1091-1100, Feb. 1, 1996.

Kierstead, H. S., "Stem Cells for the Treatment of Myelin Loss", *Trends Neurosci.*, 2005, 28(12):677-83, Epub 2005.

Kuhn, H. Georg et al., "Epidermal Growth Factor and Fibroblast Growth Factor-2 Have Different Effects on Neural Progenitors in the Adult Rat Brain", *The Journal of Neuroscience*, 17(15) 5820-5829, Aug. 1, 1997.

Kuhn, H. Georg et al., "Neurogenesis in the Dentate Gyrus of the Adult Rat: Age-Related Decrease of Neuronal Progenitor Proliferation", *The Journal of Neuroscience*, 16(6):2027-2033, Mar. 15, 1996.

Learish, Randall D. et al., "Rat Neurospheres Express mRNAs for TrkB, BDNF, NT-3 and p75", *Molecular Tools for Neuroscience*, Neural Notes Issue 19: 18-19, 2001.

Li, Jianxue et al., "Neural Stem Cells Rescue *nervous* Purkinje Neurons by Restoring Molecular Homeostasis of Tissue Plasminogen Activator and Downstream Targets", *The J. of Neuroscience*, Jul. 26, 2006, 26(30):7839-7848.

Lillen, Laura et al., "BMP and FGF Regulate the Development of EGF-responsive Neural Progenitor Cells", *Development*, 127: 4993-5005, (2000) printed in Great Britain © The Company of Biologists Limited 2000.

Littlefield, JW., Stepwise Aggregation, Compaction, and Differentiation of Uncompacted F9 Cells:, Dev. Genet. 10(5):402-10, (1989).

Mandel, RJ et al., "Progress in Direct Striatal Delivery of L-dopa via Gene Therapy for treatment of Parkinsons Disease Using Recombinant adeno-associated Viral Vectors", Exp Neurol. Sep. 1999, 159(1):47-64. Review.

Martinez-Serrano, A. et al., "Human Neural Stem and Progenitor Cells: in Vitro and in Vivo Properties, and Potential for Gene Therapy and Cell Replacement in the CNS", *Curr Gene Ther.*, 1(3):279-99, Sep. 2001, (1-Page Abstract Only).

Metz, GA. et al., The Unilaterial 6-OHDA Rat Model of Parkinson's Disease Revisited Electromyographic and Behavioural Analysis Eur. J. Neurosci. Aug. 2005, 22(3):abstract.

Mezey, Eva et al., "Turning Blood into Brain: Cells Bearing Neuronal Antigens Generated in Vivo from Bone Marrow", *Science*, 290: 1779-1782, Dec. 1, 2000.

Olson, Lars, "Grafts and Growth Factors in CNS", *Proceedings of the Xth Meeting of the World Society for Sterotactic and Functional Neurosurgery*, Maebashi, Japan, Oct. 1989, *Stereotact Funct Neutosung* 1990;54+55:250-267.

Park, Kook In et al., "Transplantation of Neural Progenitor and Stem Cells: Developmental Insights May Suggest New Therapies for Spinal Cord and Other CNS Dysfunction", *Journal of Neurotrauma*, 16(8): 675-687.

Pluchino, S et al., "Neural Stem Cells and Their use as Therapeutic Tool in Neurological Disorders", Brain Res Rev., Apr. 2005, 48(2):211-9.

Reubinoff, Benjamin E., et al., "Embryonic Stem Cell Lines from Human Blastocysts: Somatic Differentiation in Vitro", *Nature Biotechnology*, 18: 399-404, Apr. 2000.

Roitberg, Ben et al., :Cell Transplantation for Parkinson's Disease, *Neurological Research*, Jun. 2004, vol. 26, 355-362.

Shetty, Ashok, et al., "Repair of the Injured Adult Hippocampus through Graft-Mediated Modulation of the Plasticity of the Dentate Gyrus in a Rat Model of Temporal Lobe Epilepsy", *The J. of Neuroscience*, Sep. 14, 2005, 25(37):8391-8401.

Stanworth, SJ et al., "Stem Cells: Progress in Research and Edging Towards the Clinical Setting", Clin Med. Sep.-Oct. 2001, 1(5):378-82.

Svendsen, Clive N., et al., "A New Method for the Rapid and Long Term Growth of Human Neural Precursor Cells", *Journal of Neuroscience Methods*, 85: 141-152, 1998.

Svendsen, Clive N., et al, "Long-Term Survival of Human Central Nervous System Progenitor Cells Transplanted into a Rat Model of Parkinson's Disease", *Experimental Neurology*, 148: 135-146, 1997.

Tagagi, Yasushi et al., "Dopaminergic Neurons Generated from Monkey Embryonic Stem Cells Function in a Parkinson Primate Model", *The J. of Clinical Investigation*, Jan. 2005, 115(1):102-109.

Thomas, CE et al., "Progress and Problems with the use of Viral Vectors for Gene Therapy", Nat Rev Genet. May 2003, 4(5):346-58.

Thomson, James A. et al., "Embryonic Stem Cell Lines Derived from Human Blastocysts", *Science*, 282: 1145-1147, Nov. 6, 1998.

Tropepe, Vincent et al., "Distinct Neural Stem Cells Proliferate in Response to EGF and FGF in the Developing Mouse Telencephalon", *Developmental Biology*, 208: 166-188, 1999.

Van Leeuwan, J. et al., "Role of Extracellular calcium in the regulation of 1, 25-dihdroxyvitamin D3 formation in . . . ," Biochimica et Biophysics Acta, 1221:167-170 (1994).

Winkler, Christian et al., "Incorporation and Glial Differentiation of Mouse EGF-Responsive Neural Progenitor Cells after Transplantation into the Embryonic Rat Brain", *Molecular and Cellular Neuroscience*, 11: 99-116, 1998.

Wobus, AM et al., "Embryonic Stem Cells: Prospects for Developmental Biology and Cell Therapy", Physiol. Rev. Apr. 2005, 85(2)635-78.

Wolf, JA et al., "Grafting Fibrobalasts Genetically Modified to Produce L-dopa in a Rat Model of Parkinson's Disease", Proc. Natl. Acad. Sci., USA, Nov. 1989, 86(22):9011-4.

Yasuhara, Takao et al., "Transplantation of Human Neural Stem Cells Exerts Neuroprotection in a Rat Model of Parkinson's Disease:", *The J. of Neuroscience*, Nov. 29, 2006, 26(48):12497-12511.

Zhou, F.C., et al., "Long-term Nonpassaged EGF-responsive Neural Precursor Cells are Stem Cells", *Wound Repair and Regeneration*, 6(4):S-337-S-348, 1998.

Zhou, F.C., et al., "Three to Four-year-old Nonpassaged EGF-responsive Neural Progenitor Cells: Proliferation, Apoptosis, and DNA Repair", *Exp Neurol*, 164(1):200-8, 2000, (1-Page Abstract Only).

Online Product search results for basic FGF, R & D Systems, printed Apr. 11, 2007. p. 1.

Online Product search results for TGF alpha, R & D Systems, printed Apr. 11, 2007. p. 1.

Online Product search results for EGF, R & D Systems, printed Apr. 11, 2007. p. 1.

Online Literature for GIBCO Advanced D-MEM/F-12, printed Apr. 11, 2007, pp. 1-2.

USPTO Office Action mailed on Apr. 20, 2009 in parent U.S. Appl. No. 11/755,224, filed May 30, 2007 13pp.

USPTO Office Action dated May 18, 2009 re related patent U.S. Appl. No. 11/002,933, filed Dec. 2, 2004 7pp.

USPTO Office Action mailed on Mar. 31, 2008 from related patent U.S. Appl. No. 11/002,933, filed Dec. 2, 2004 28pp.

USPTO Office Action mailed on Oct. 5, 2007 from related patent U.S. Appl. No. 11/002,933, filed Dec. 2, 2004 35pp.

USPTO Office Action mailed on Apr. 23, 2007 from related patent U.S. Appl. No. 11/002,933, filed Dec. 2, 2004 27pp.

USPTO Office Action mailed on Aug. 24, 2006 from related patent U.S. Appl. No. 11/002,933, filed Dec. 2, 2004 13pp.

USPTO Office Action mailed on Feb. 27, 2006 from related patent U.S. Appl. No. 11/002,933, filed Dec. 2, 2004 14pp.

* cited by examiner

Fig. 14. BrDU-positive cells in M5 line suspension. DAB staining. 40x

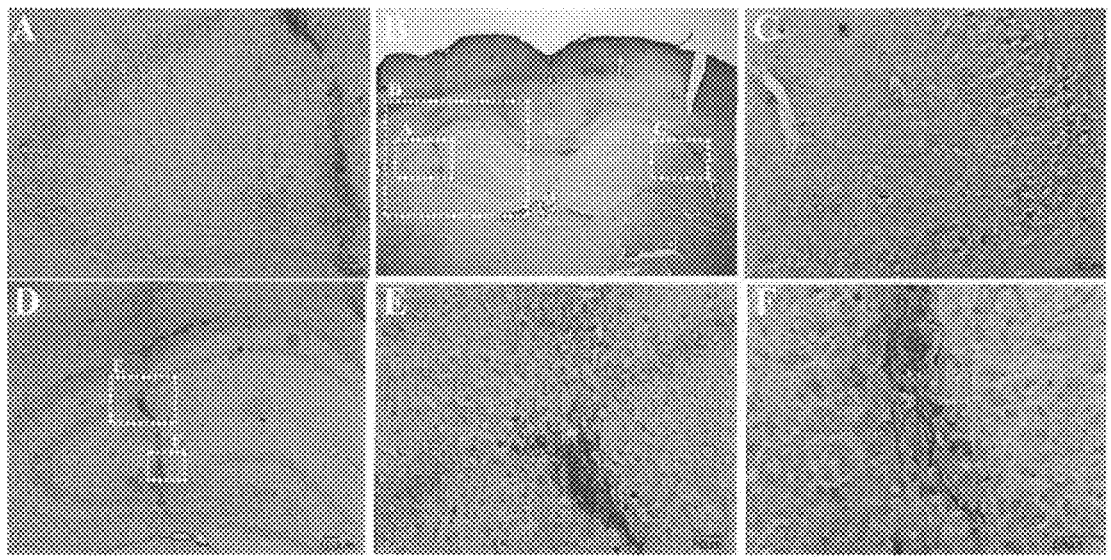
Fig. 23
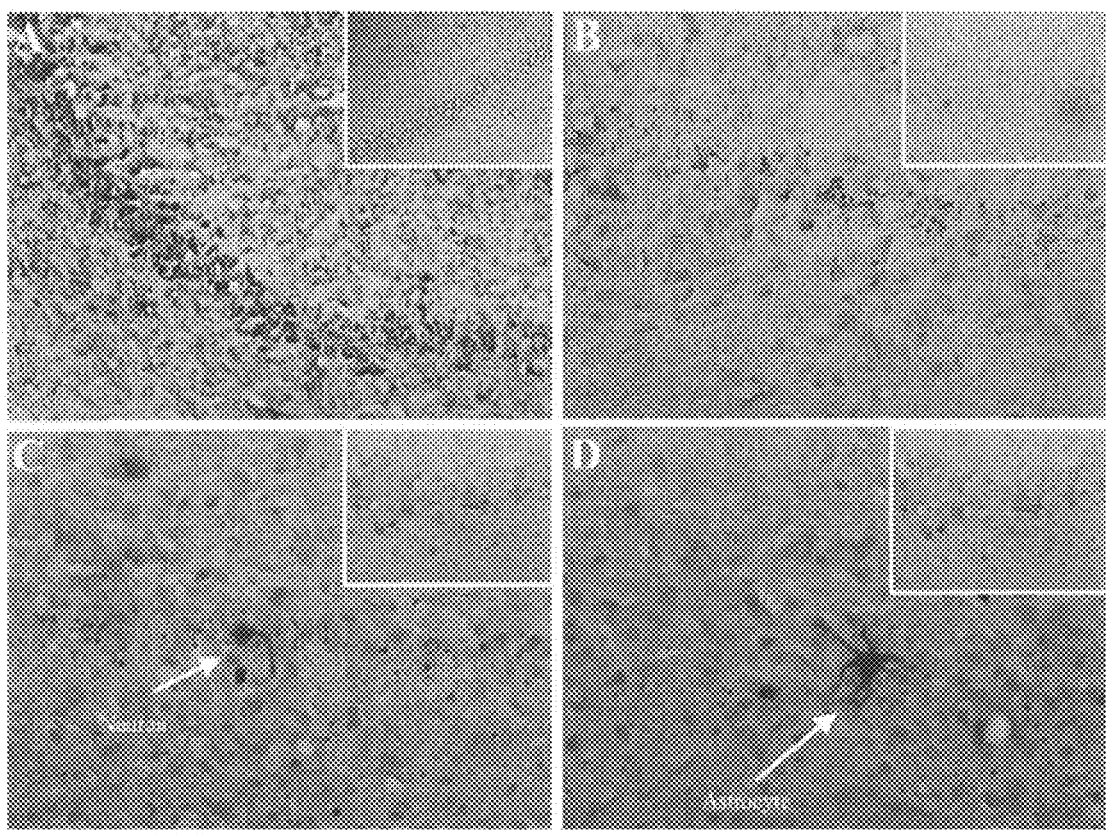
Fig. 24A-D

PLURIPOTENT CELLS

This application is a divisional of U.S. patent application Ser. No. 11/755,224, filed May 30, 2007, now abandoned, which claims the benefit of provisional patent application No. 60/803,619, filed May 31, 2006; and is a continuation-in-part of U.S. patent application Ser. No. 11/002,933, filed Dec. 2, 2004, now U.S. Pat. No. 7,632,681, issued Dec. 15, 2009, which claims priority to provisional application No. 60/526,242, filed Dec. 2, 2003, the entire contents of each of which are incorporated by reference herein. Throughout this application various publications are referenced. The disclosures of these publications in their entireties are hereby incorporated by reference into this application in order to describe more fully the state of the art to which this invention pertains.

BACKGROUND OF THE INVENTION

Parkinson's disease (PD) is a very common neurodegenerative disorder that affects more than 2% of the population over 65 years of age. PD is caused by a progressive degeneration and loss of dopamine (DA)-producing neurons, which leads to tremor, rigidity, and hypokinesia (abnormally decreased mobility). It is thought that PD may be the first disease to be amenable to treatment using stem cell transplantation. Factors that support this notion include the knowledge of the specific cell type (DA neurons) needed to relieve the symptoms of the disease. In addition, several laboratories have been successful in developing methods to induce embryonic stem cells to differentiate into cells with many of the functions of DA neurons.

While attempts have been made to propagate neural progenitor cells (partially differentiated precursors to neurons and glial cells) for use in neurotransplantation and for drug screening, these efforts have met with limited success. Neurobasal medium has allowed for fast doubling times of cultured neural progenitor cells, but these doubling times are observed for about one month, after which the cells differentiate and lose their progenitor phenotype. Typically, with the most optimal culture conditions, neural progenitor cells will survive for only about 10 passages in culture. In addition, only about 1-2% of neural progenitor cells survive cryopreservation. Moreover, current efforts to maintain neural progenitor cells in vitro require the use of a feeder layer and/or introduce animal components. Even with use of a feeder layer, neural progenitor cells have been maintained for only about 6 months. For clinical applications, it is desirable to obtain and maintain human neural progenitor cells that are free of animal components and do not require the use of a feeder layer.

Likewise, the development of stem cells for transplantation has been approached with an assumption that such pluripotent cells would have to be genetically modified in order to express the desired phenotype for therapeutic benefit, such as the neurotransmitter dopamine for treatment of Parkinson's disease. Alternatively, it has been assumed that one must expose the stem cells to conditions that would induce predifferentiation to achieve the desired phenotype.

There remains a need for a large quantities of undifferentiated neural progenitor cells and pluripotent or totipotent stem cells for transplantation and for drug screening, particularly for human progenitor and stem cells. A need also exists for cells that are capable of long-term proliferation in vitro. In particular, there is a need for methods of maintaining and propagating neural progenitor and pluripotent cells for extended periods of time, and for methods that optimize yield following cryopreservation.

SUMMARY OF THE INVENTION

The invention provides pluripotent cells that can be propagated and maintained for extended periods of time in culture in the absence of a feeder layer. Surprisingly, these cells express both markers for partially differentiated neural progenitor cells (nestin, SSEA-1) and markers for pluripotent stem cells (TRA-1-60, TRA-1-81, SSEA-4, Oct-4). Also provided are methods of propagating and using such cells. These cells are useful for transplantation to hosts having disease and/or damage, particularly of the central nervous system, as they are capable of migrating to the sites in need of repair, and of adopting a phenotype most appropriate to the nature of the damage or disease. Moreover, the pluripotent cells of the invention have been found to have a surprising ability to protect against massive structural and functional damage.

The pluripotent nature of these cells renders it unnecessary to genetically modify the cells to be transplanted, and also obviates concerns about selecting the appropriate phenotype of cells, or predifferentiating cells prior to transplantation. Accordingly, the invention provides, in one embodiment, a substantially pure culture of pluripotent cells that is free of genetically modified cells. Use of these pluripotent cells provides particular advantages for transplantation and therapy over, for example, use of predifferentiated cells.

BRIEF DESCRIPTION OF THE FIGURES

FIG. 23 is a series of photomicrographs taken of histological sections from hippocampus (Panel B) at day 10 following intraventricular injection of PC of the invention in rats subjected to unilateral kainic acid lesions of the hippocampus (an animal model of epilepsy). Immunostaining with antibodies to human nestin shows that these transplanted PC exhibit purposeful migration to the damaged hippocampus, shown in panels A, D, E and F, and no migration to the healthy, contralateral, hippocampus (Panel C).

FIG. 24A-D is a series of photomicrographs taken of histological sections from hippocampus showing multi-lineage differentiation of PC implanted in the rat model of epilepsy.

Figure 1:
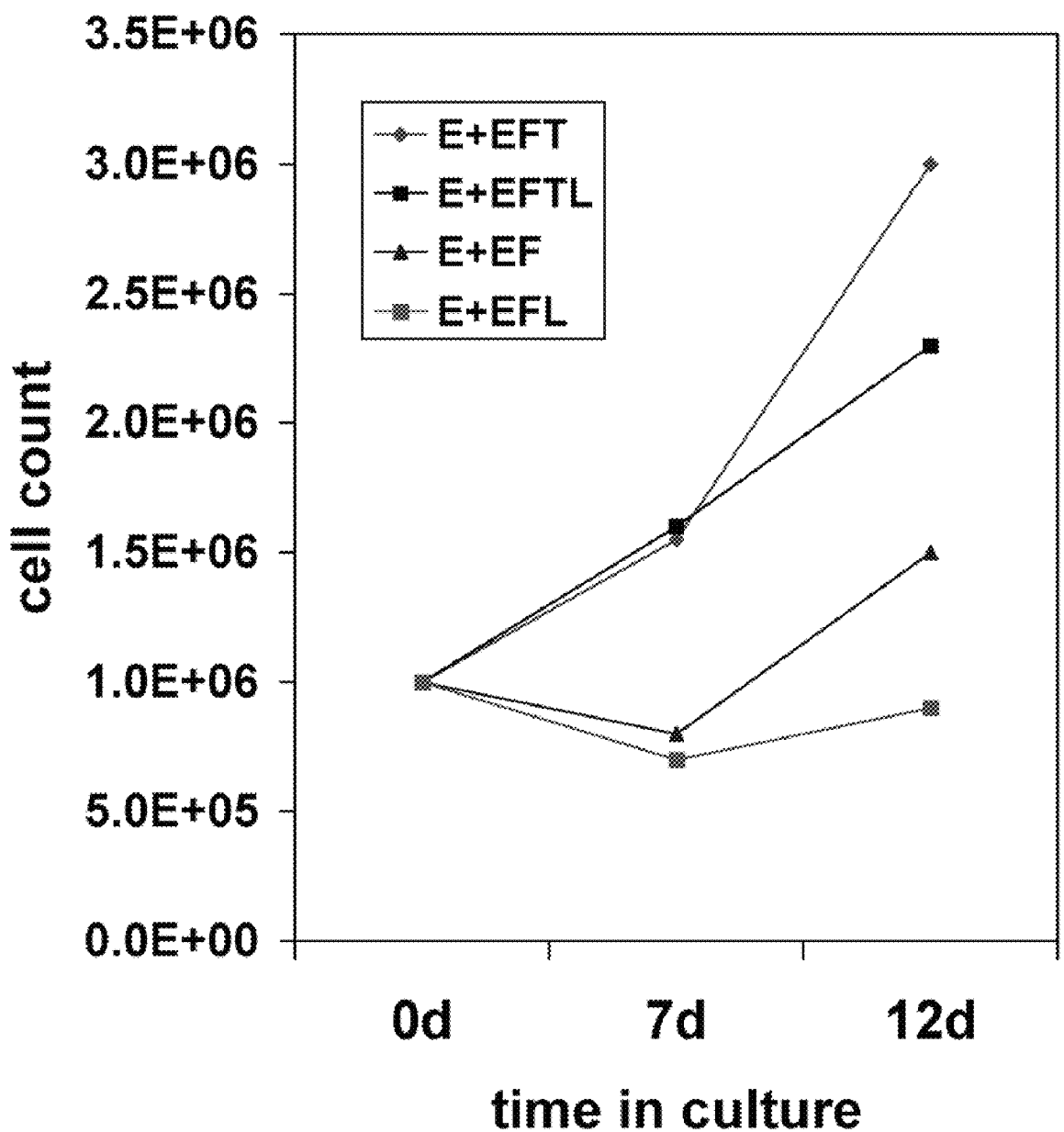
FIG. 1 is a graph showing the growth of cultured NPC in low calcium (0.06 mM) EMEM supplemented with ("E+") various combinations of EGF (E), bFGF (F), TGFα (T) and LIF (L). E+EFT provided optimal growth of NPC in suspension.
Figure 2:
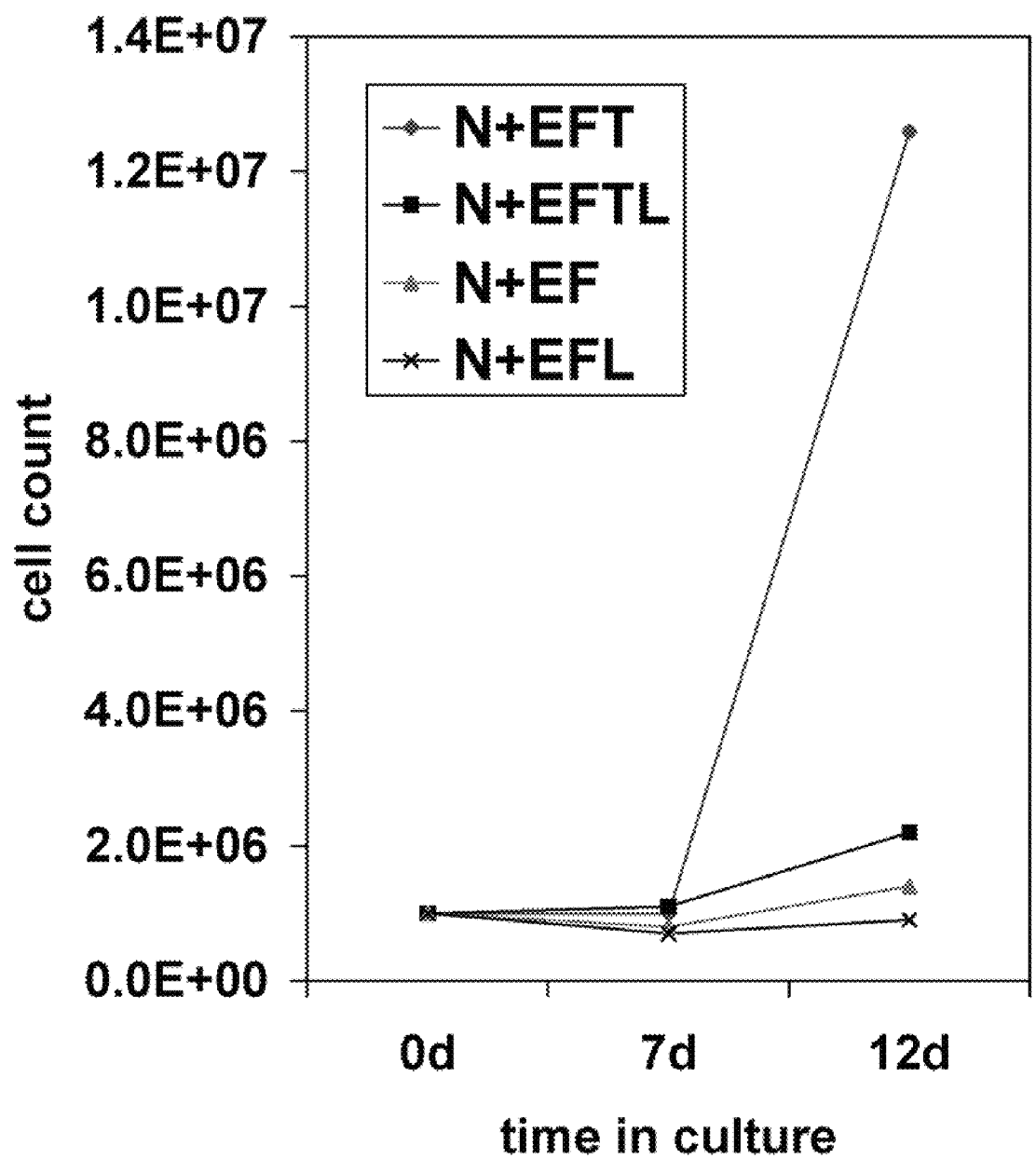
FIG. 2 is a graph showing the growth of cultured NPC in Neurobasal™ medium supplemented with (N+) various combinations of EGF (E), bFGF (F), TGFα (T) and LIF (L). N+EFT provided optimal growth of attached cells. Growth rates declined, however, after 3-4 months in vitro.
Figure 3:
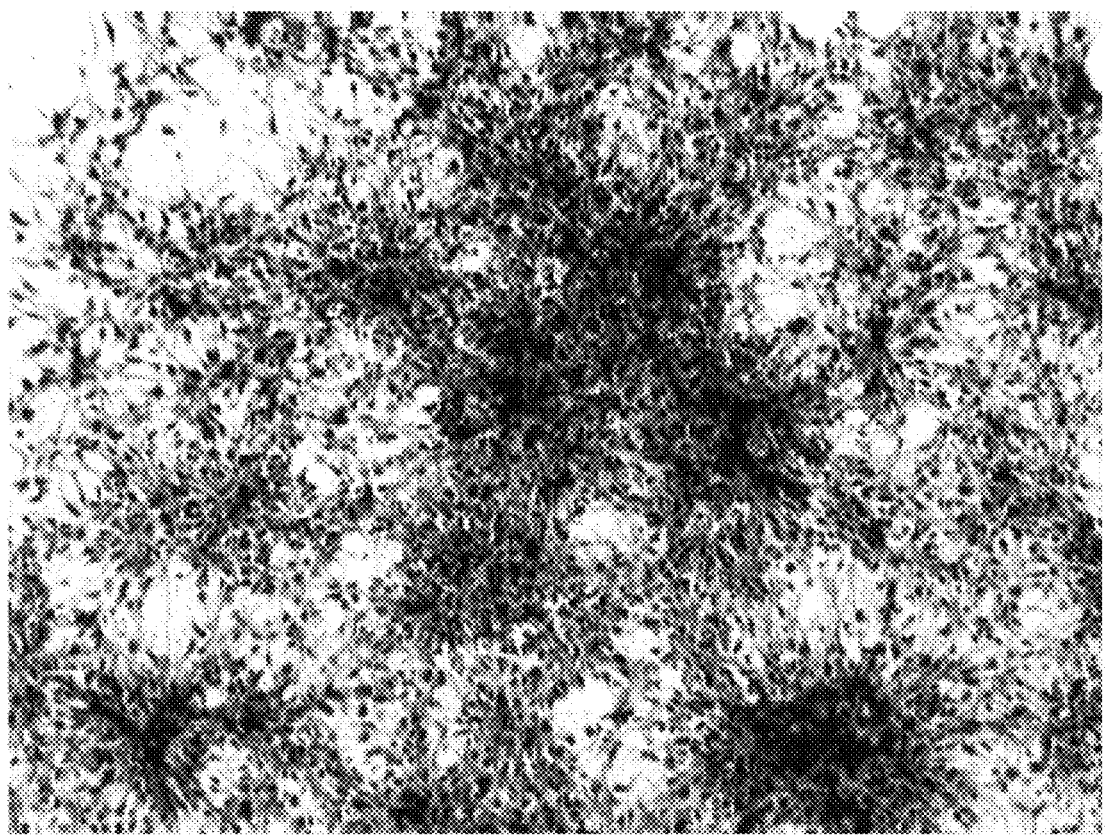
FIG. 3 is a photomicrograph showing immunohistochemistry of T and M brain progenitor lines. A strong BrDU-positive reaction was observed in the M5 line cells after 138 passages. 20× magnification.

Panel A shows immunostaining with antibodies to human mitochondria at 10 days after PC injection into the ventricle, where human PC repopulated the damaged CA3 zone of the hippocampus. Panel B shows immunostaining with antibodies to the inhibitory neurotransmitter, GABA, at 16 days after PC injection, showing that PC differentiate into inhibitory GABAergic neurons to counteract the epileptogenic hippocampus. Panels C & D show immunostaining with antibodies to human mitochondria at 10 days after PC injection, showing human PC have differentiated into both neurons and astrocytes. The inserts at each panel show the contralateral hippocampus, which is free of transplanted PC.

DETAILED DESCRIPTION OF THE INVENTION

The present invention is based on the discovery of an unexpected type of pluripotent cells (PC) and a culture medium optimized for long-term growth of these cells, which express markers of both human neural progenitor cells (NPC) and stem cells. The invention also relates to successful cryopreservation of NPC/PC. PC cultured in accordance with the invention are capable of surviving in vitro for longer than one year, and as long as three and a half years. Cryopreservation of PC in accordance with the invention results in over 95% viability upon thawing. In addition, the invention provides variations on the culture medium that allow for manipulation of the cultured PC to achieve attachment and differentiation when desired. PC cultured in accordance with the invention have been successfully transplanted into the brain, providing restoration of structure and function in an animal model of Parkinson's disease and in an animal model of epilepsy. In addition, PC implanted simultaneously with or shortly after the seizure-inducing lesion protect the brain from structural damage and prevent seizure activity.

Definitions

All scientific and technical terms used in this application have meanings commonly used in the art unless otherwise specified. As used in this application, the following words or phrases have the meanings specified.

As used herein, "low calcium" medium refers to less than 0.15 mM calcium (final concentration), and typically about 0.03-0.09 mM. Low calcium medium does not include calcium-free medium. "High calcium" medium refers to greater than 0.15 mM calcium.

As used herein, "neural progenitor cell" (NPC) refers to cells that are immunopositive for nestin, capable of continuous growth in suspension cultures and, upon exposure to appropriate conditions, can differentiate into neurons or glial cells. A neural progenitor cell, as referred to herein, is capable of surviving for at least 2-3 years in vitro. SSEA-1 is also a marker for NPC.

As used herein, "pluripotent cell" (PC; or pluripotent stem cell, PSC) refers to cells that are immunopositive for the pluripotent cell markers, TRA-1-60, TRA-1-81, SSEA4, and Oct-4.

As used herein, "genetically modified" refers to cells that have been manipulated to contain a non-native transgene by recombinant methods. For example, cells can be genetically modified by introducing a nucleic acid molecule that encodes a selected polypeptide.

As used herein, "transgene" means DNA that is inserted into a cell and that encodes an amino acid sequence corresponding to a functional protein. Typically, the encoded protein is capable of exerting a therapeutic or regulatory effect.

As used herein, "protein" or "polypeptide" includes proteins, functional fragments of proteins, and peptides, whether isolated from natural sources, produced by recombinant techniques or chemically synthesized. Polypeptides typically comprise at least about 6 amino acids, and are sufficiently long to exert a biological or therapeutic effect.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, Remington's Pharmaceutical Sciences, 18th edition, A. Gennaro, ed., Mack Publishing Co., Easton, Pa., 1990).

As used herein, "a" or "an" means at least one, unless clearly indicated otherwise.

Pluripotent Cells

The invention provides pluripotent cells (PC) that can be maintained indefinitely in culture, stain positively for bromodeoxyuridine (BrdU), TRA-1-60, TRA-1-81, SSEA-4, SSEA-1, Oct-4 and nestin, and are multipotent. The PC of the invention are capable of generating neurons (e.g., MAP2, neuron specific enolase or neurofilament positive cells) and glia (e.g., GFAP or galactocerebroside positive cells), as well as other cell types. PC of the invention can be maintained in cell culture, typically as a suspension culture, for at least one year. The PC described herein have been maintained for as long as three years.

The PC of the invention exhibit 50% growth in the first 2 days in culture, and doubling times of less than 10 days, typically about 6 days. Doubling times of as little as 5 days have been observed. In addition, these cells continue to grow in culture for extended periods of time. Unlike NPC cultured in conventional media such as Neurobasal™ medium, however, these cultures do not show a decline after 3-4 months, but continue to survive and expand for years, and through hundreds of passages.

Figure 4:
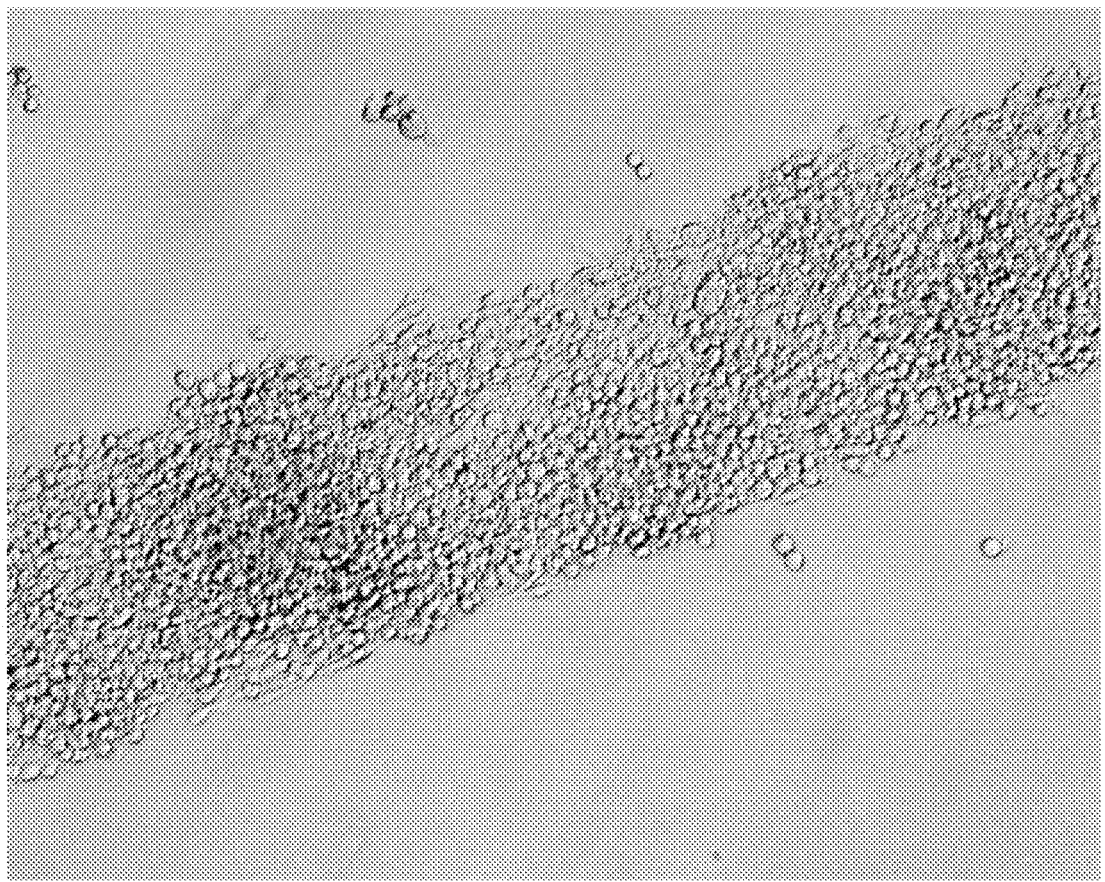
FIG. 4 is a phase contrast photomicrograph that shows a confluent growth of M5 NPC cells. Almost all cells maintain undifferentiated condition. 10× magnification.
Figure 5:
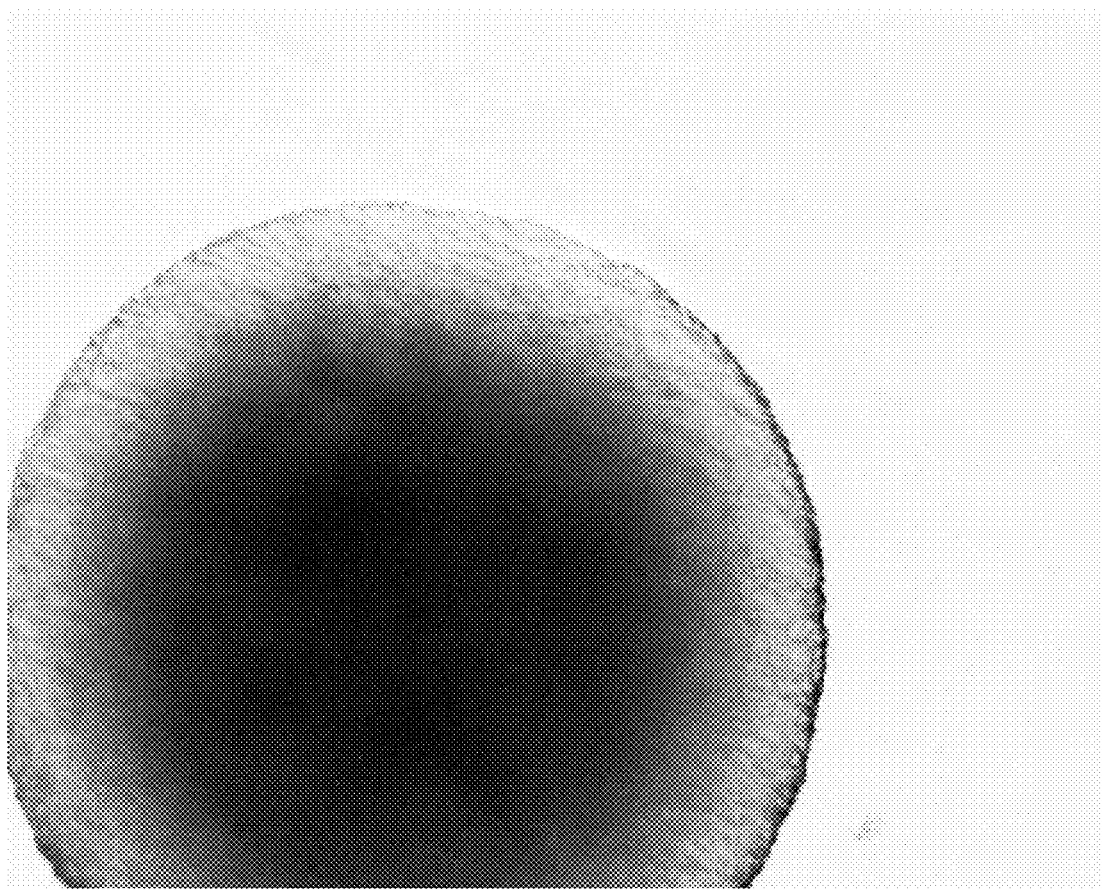
FIG. 5 is a phase contrast photomicrograph that shows a typical "embryoid body" formed by the brain progenitor cells and characteristic for stem/progenitor cells. 10× magnification.
Figure 6:
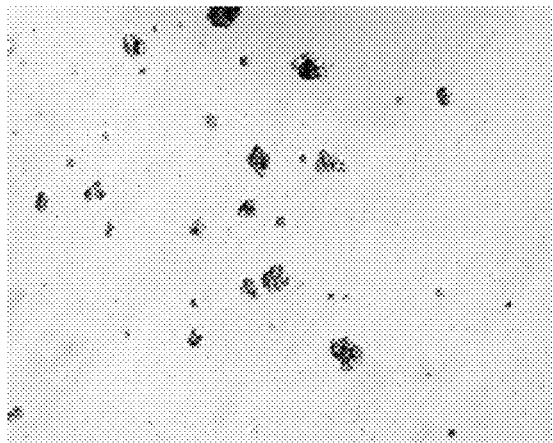
FIG. 6 is a phase contrast photomicrograph that shows brain progenitor cells from the 5$^{th}$ passage of T5 line growing in small floating clusters. 10× magnification.
Figure 12:
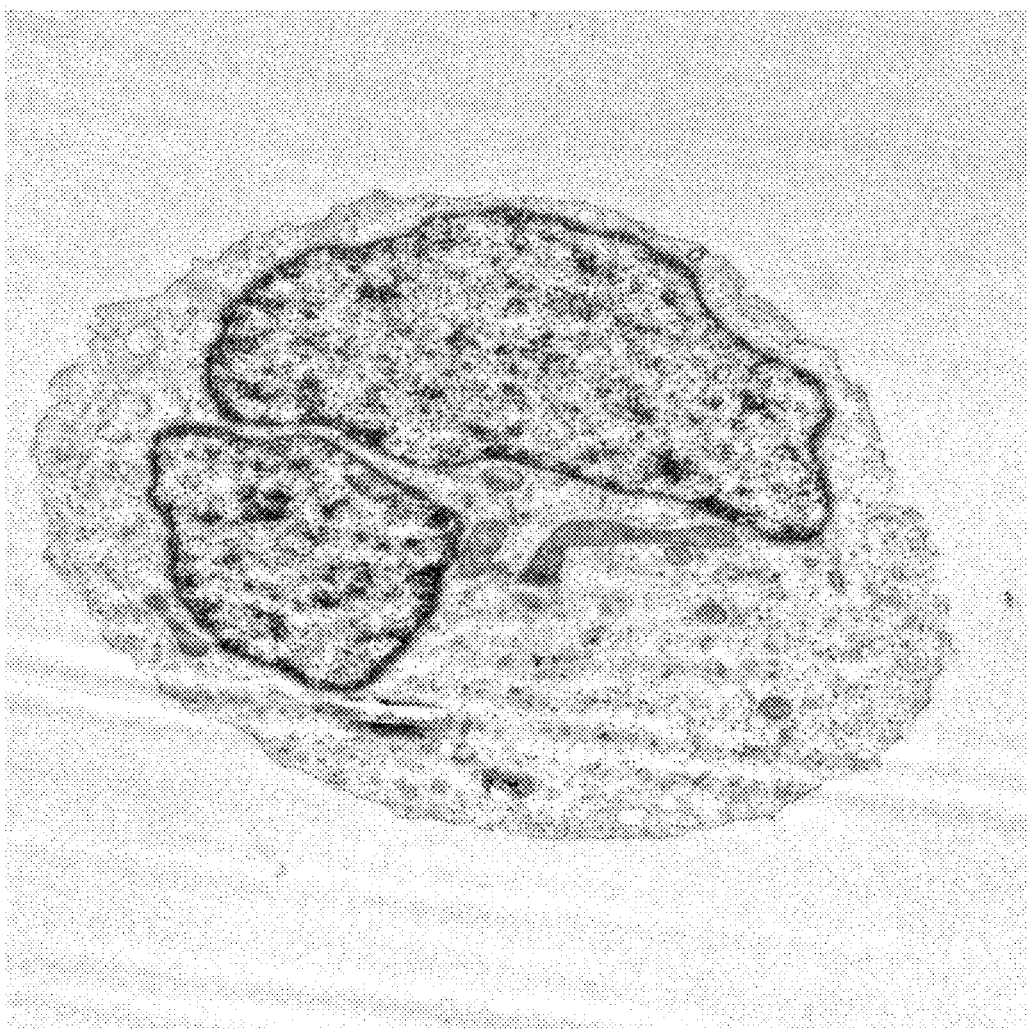
FIG. 12 is an electron micrograph showing the ultrastructure of an undifferentiated NPC from T5 line. 13,000× magnification.
Figure 13:
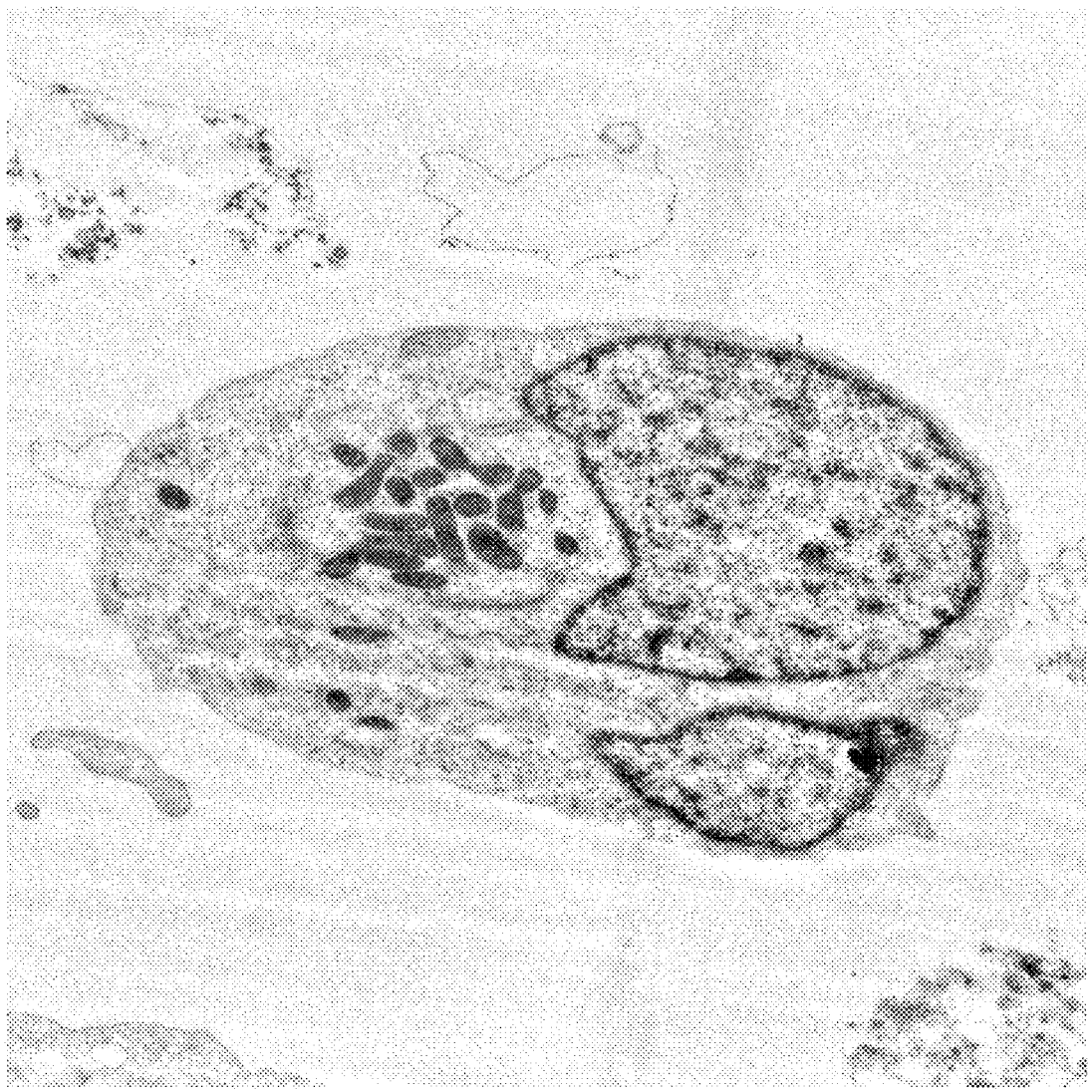
FIG. 13 is an electron micrograph showing the ultrastructure of a NPC from M5 line. Its cytoplasm contains many mitochondria. 13,000× magnification.
Figure 14:
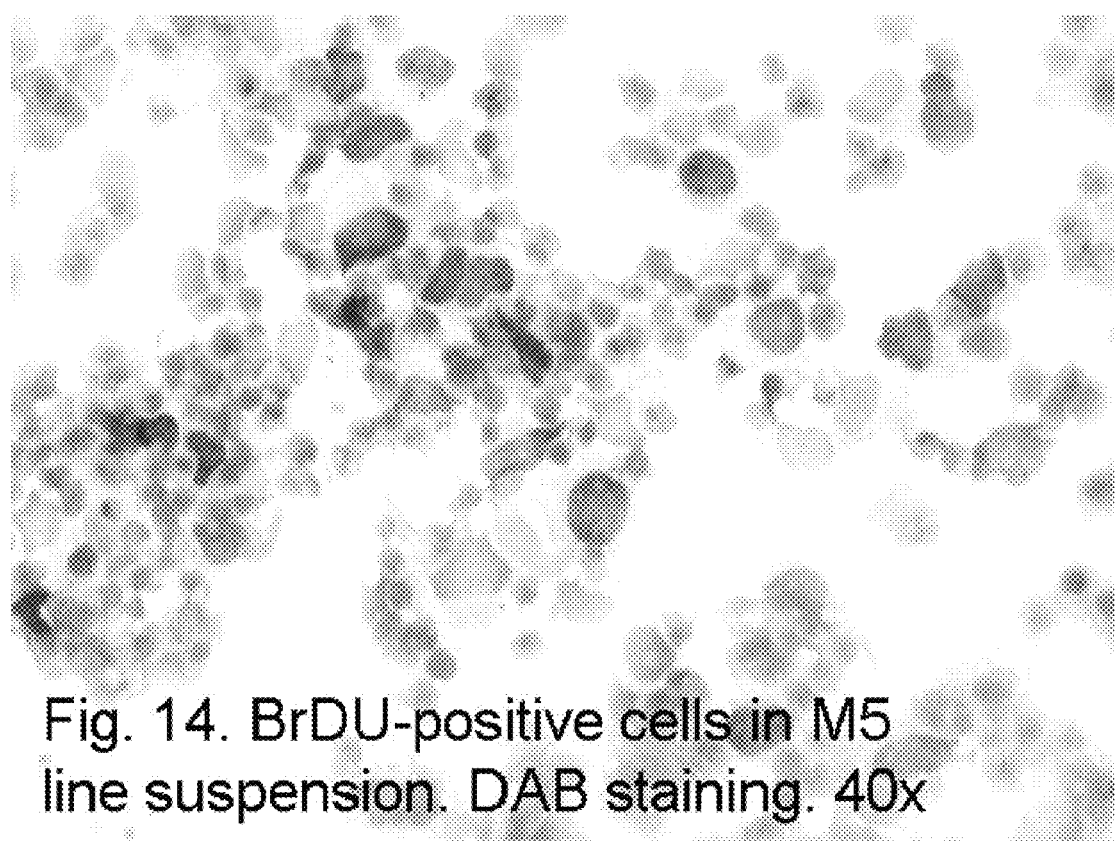
FIG. 14 is a photomicrograph showing bromodeoxyuridine (BrDU) immunopositive NPC in a M5 line suspension. Immunoreactive cells stained with diaminobenzidine (DAB). 40× magnification.
Figure 15:
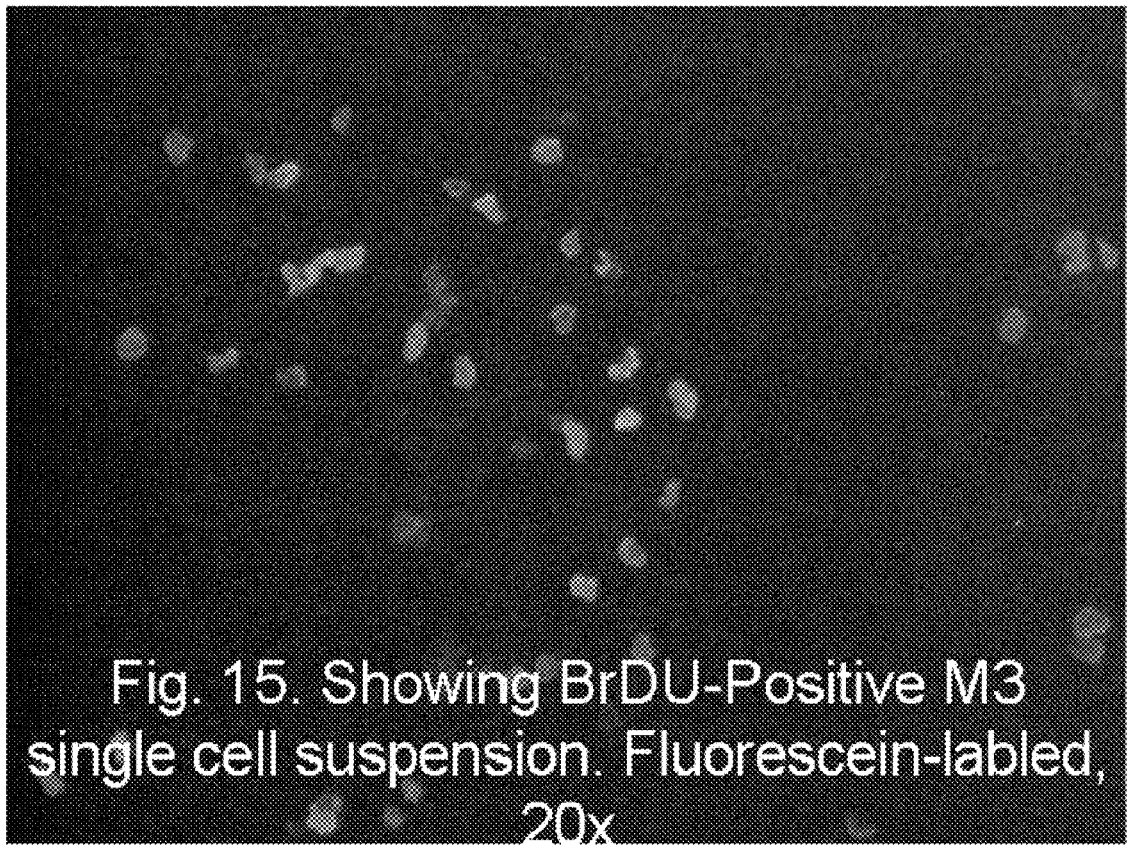
FIG. 15 is a photomicrograph showing bromodeoxyuridine (BrDU) immunopositive NPC in a M3 single cell suspension. Immunoreactive cells labeled with fluorescein. 20× magnification.
Figure 16:
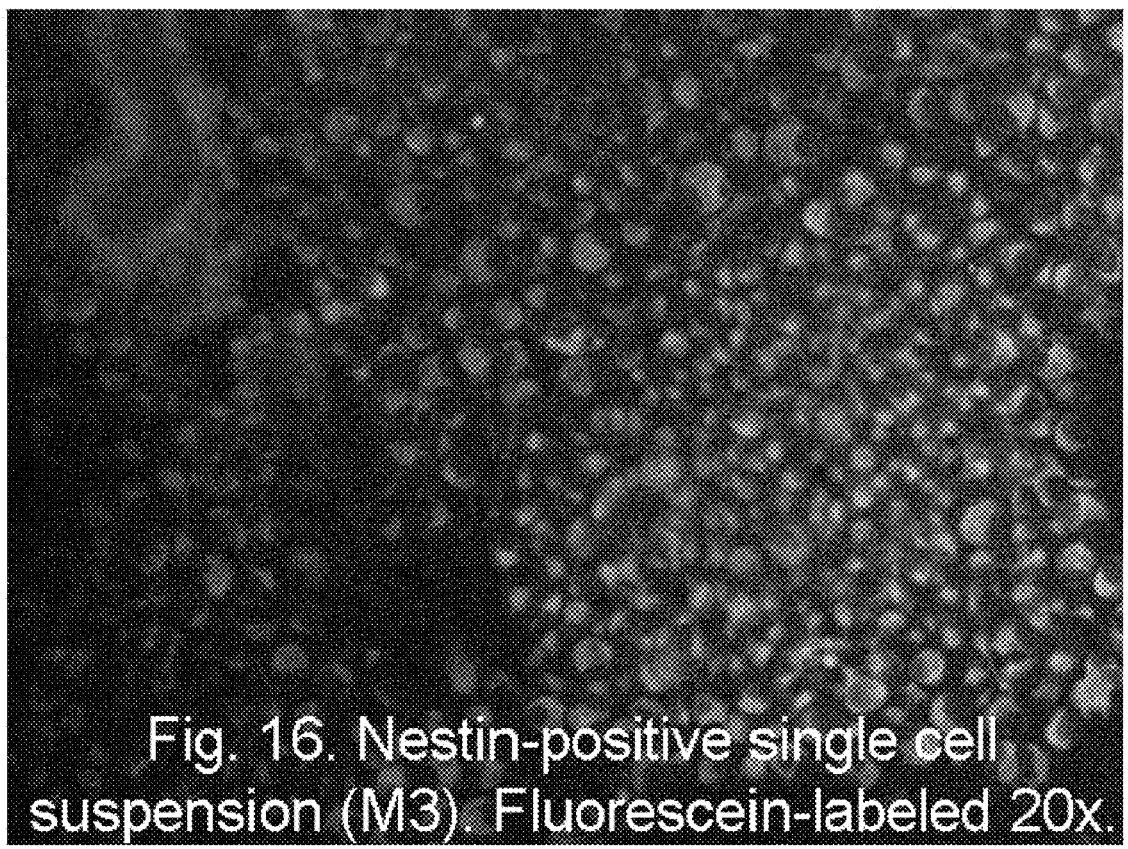
FIG. 16 is a photomicrograph showing nestin immunopositive NPC in a M3 single cell suspension. Immunoreactive cells labeled with fluorescein. 20× magnification.

In addition, the PC of the invention exhibit normal structure and function that is typical of progenitor cells. As shown in FIG. 5, PC form embryoid bodies in culture. FIG. 4 shows a confluent growth of PC that remain undifferentiated, and FIG. 6 shows PC growing in floating clusters. FIGS. 12 and 13 are electron micrographs, showing the normal ultrastructure of PC of the invention.

PC can be prepared from mesencephalon and/or telencephalon of fetal brain, as described in Example 1 below. Typically, the tissue is dissected in a general purpose serum-free medium, such as Hank's Balanced Salt Solution (HBSS) with 0.25 μg/ml of Fungizone and 10 μg/ml of Gentamicin, under sterile conditions.

The cultures described herein will initially include a small percentage of Oct-4-positive cells, and mostly nestin-positive NPC cells. Over a period of months in culture, the proportion of Oct-4-positive cells increases significantly. For example, a typical culture will shift from being 5% Oct-4-positive cells to up to 30% Oct-4-positive cells in four months.

The PC of the invention can be used in all the ways described herein for NPC. The Oct-4-positive status of these cells indicates that they are capable of many additional uses beyond the neural environment. The pluripotent nature of these cells make them attractive for placement in a variety of tissue environments, wherein local cytokines (natural and/or exogenously supplied) and other signals induce appropriate differentiation and migration. In the description of methods that follows, it is understood that NPC refers to NPC and/or PC.

Media and Methods for Cell Culture

Figure 7:
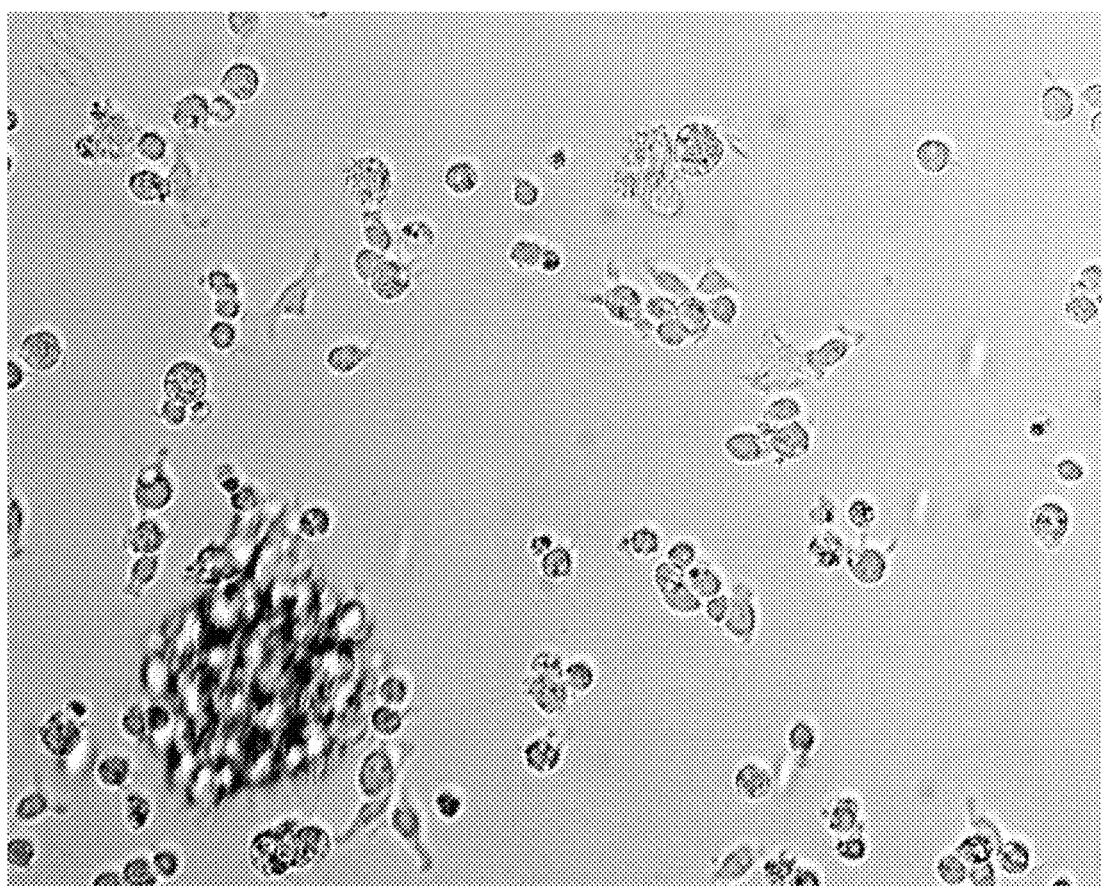
FIG. 7 is a phase contrast photomicrograph that shows a small floating cluster of the NPC and a number of the NPC cells that are getting attached to the culture flask due to the increase in medium Ca++ concentration from 0.05 mMol to 0.1 mMol. 10× magnification.
Figure 8:
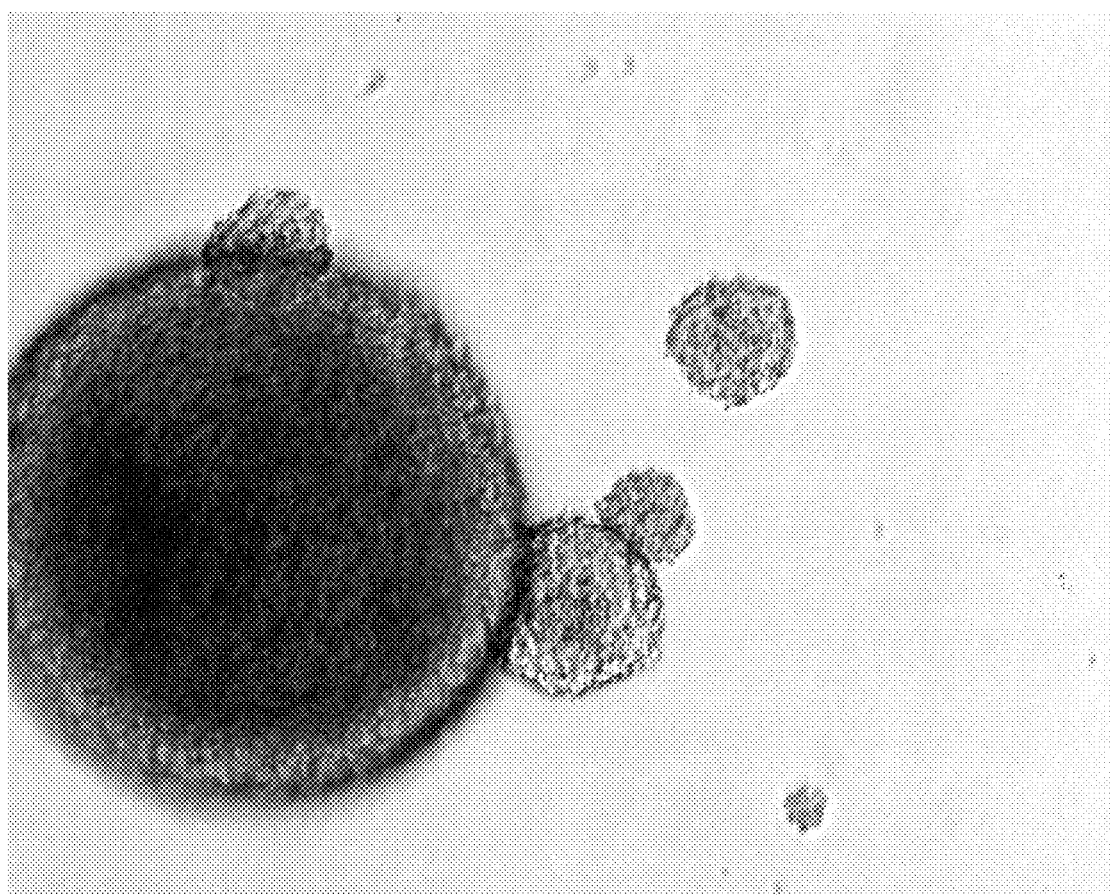
FIG. 8 is a phase contrast photomicrograph that shows the NPC from T5 line growing as embryoid bodies. 154$^{th}$ passage. 10× magnification.
Figure 9:
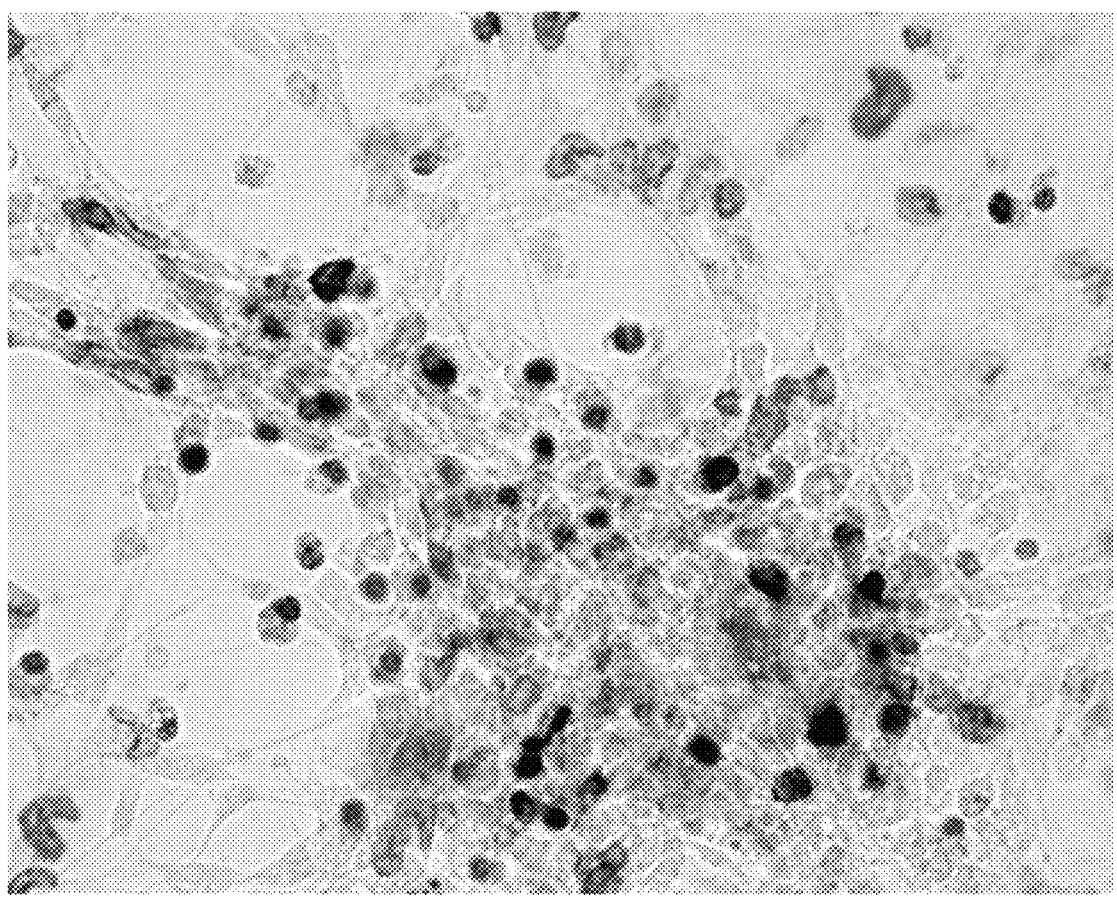
FIG. 9 is a photomicrograph showing a flat cluster of the NPC from M5 line. Ca++ concentration of the culture medium at 0.1 mMol. 46% of the cells are BrDU-positive. 20× magnification.
Figure 10:
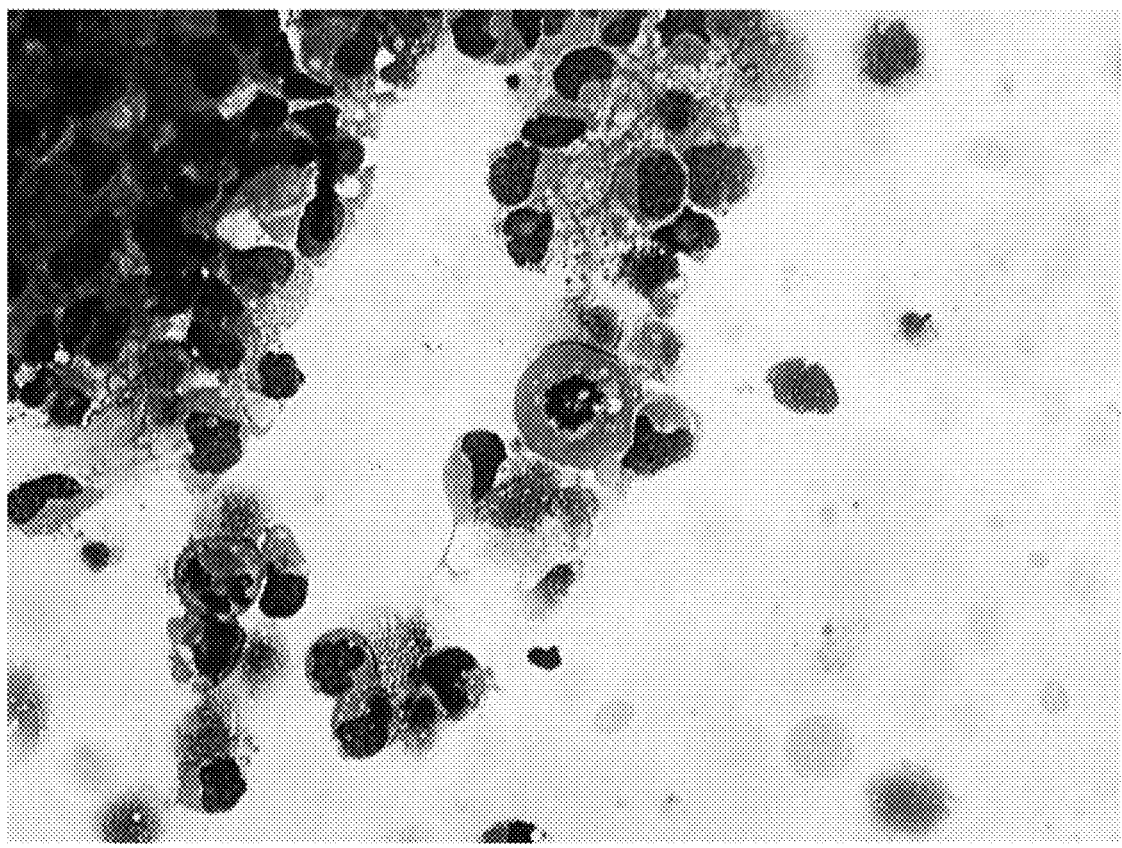
FIG. 10 is a photomicrograph showing a large floating cluster of cells from T5 line, with a mitotic figure in the center. Giemza stain. 40× magnification.
Figure 11:
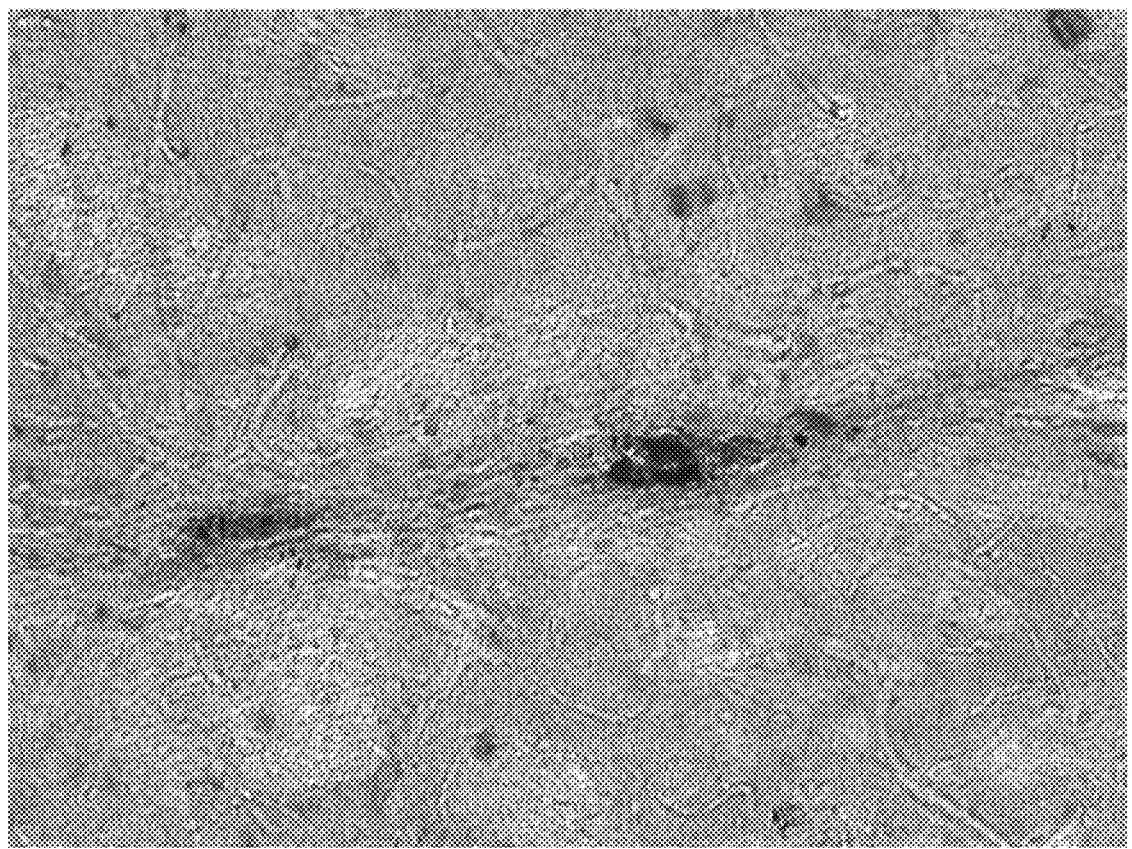
FIG. 11 is a photomicrograph showing the tyrosine hydroxylase (TH)-positive NPCs in the striatum of a 6-OHDA lesioned rat. 20× magnification.

The structure and function of PC in culture is subject to manipulation via the culture medium. For example, raising the calcium concentration of the medium from 0.05 mM to 0.1 mM leads to attachment of the progenitor cells to the culture flask (see FIG. 7). The addition of LIF to the culture medium extends the doubling time, but allows for a higher population of neurons. Addition of LIF also helps to prevent formation of large clusters of PC. TGFα in the medium serves to significantly reduce doubling time (e.g., from 14 days to 5 days). Accordingly, the culture medium is selected in accordance with the particular objectives, with some ingredients favoring growth and expansion and other ingredients favoring attachment and differentiation.

For general purposes, the cell culture requires a low calcium basal medium (e.g., Ca++ free EMEM supplemented with calcium chloride), typically a B27 or equivalent supplement, and growth factors (e.g., EGF, FGF, TGFα). Optional ingredients include L-glutamine and LIF, which promote growth of neurons.

Example 3 below provides a detailed description of the optimization of culture media for expansion and for differentiation of PC. In general, long-term growth and expansion requires a low calcium concentration. This is typically achieved by use of a calcium-free minimum essential medium (EMEM) to which calcium is added. Optimal growth and expansion has been observed at calcium concentrations of 0.05-0.06 mM. As the calcium concentration rises, e.g., above 0.15 mM, network formations between the neurons in culture are observed as they take on a more differentiated neuronal phenotype. In these higher calcium cultures, only 1-2% of the cells are immunopositive for the astrocytic marker GFAP, even without the addition of LIF to the culture medium.

The following table summarizes the range of concentrations suitable for culture medium components:

| Component: | Concentration: |
|---|---|
| B27 | 0.5-2.5% |
| Calcium Chloride | 0.05 mM-0.12 mM |

-continued

| Component: | Concentration: |
| --- | --- |
| Epidermal Growth Factor | 15 ng/µL-100 ng/µl |
| Basic Fibroblast Growth Factor | 10 ng/µL-150 ng/µL |
| Transforming Growth Factor Alpha | 10 ng/µL-75 ng/µL |
| Leukemia Inhibitory Factor | 25 ng/µl-150 ng/µl |
| L-Glutamine | 0.1 mM-0.7 mM |
| N2 Supplement | 0.3%-2.0% |

NPC are typically grown in suspension cultures. Initial plating of primary cells was optimal at 30,000 to 50,000 cells/cm$^2$. Medium changes can be made every 6 days by removing the cells to a test tube and spinning (e.g., 5 min at 1,500 rpm). Typically, all but 2 ml of the original medium is discarded and the pellet is resuspended in the remaining 2 ml of original medium combined with an additional 3 ml of fresh medium. When density exceeds 400,000 cells/ml, the cells can be split into two culture vessels (e.g., T75 flasks). Trituration of the cells at the time of feeding helps to break up clusters of NPC and maintain their suspension in the culture medium. Those skilled in the art will appreciate that variation of these parameters will be tolerated and can be optimized to suit particular objectives and conditions.

The PC of the invention can be used in therapeutic and diagnostic applications, as well as for drug screening and genetic manipulation. The PC and/or culture media of the invention can be provided in kit form, optionally including containers and/or syringes and other materials, rendering them ready for use in any of these applications.

Cryopreservation of PC

The invention provides optimized methods and media for freezing and thawing of NPC and PC. The ability to store and successfully thaw NPC and PC is valuable to their utility in clinical applications and ensuring a continued and consistent supply of suitable cells. While most experts working with progenitor and pluripotent cell populations observe only a 2-30% survival of cells after freeze-thaw, the present invention offers media and methods that result in over 50% survival following freeze-thaw, with viability typically greater than 95%.

For cryopreservation, PC (or NPC) are suspended in a low calcium medium supplemented with B27 and DMSO, and the trophic factors used in the expansion culture medium. Typically, the growth factors in the cryopreservation medium comprise about 20-100 ng/ml epidermal growth factor (EGF); about 10-50 ng/ml fibroblast growth factor basic (bFGF); and about 1-150 ng/ml transforming growth factor-alpha (TGFα). For thawing, both the culture medium and the flask, or other vessel into which the cells will be grown, are pre-warmed to 15-40° C., preferably to approximately 25-37° C. Typically, culture flasks (or other vessel) are pre-warmed in an incubator with the same or similar gas, humidity and temperature conditions as will be used for growing the cells. For example, typical temperature is about 37° C., and typical $CO_2$ level is about 5% (and $O_2$ the remaining 95%).

Therapeutic Use of Pluripotent Cells

The PC of the invention can be implanted into the central nervous system (CNS) of a host using conventional techniques. Neural transplantation or "grafting" involves transplantation of cells into the parenchyma, into the ventricular cavities or subdurally onto the surface of a host brain. Conditions for successful transplantation include: 1) viability of the implanted cells; 2) formation of appropriate connections and/or appropriate phenotypic expression; and 3) minimum amount of pathological reaction at the site of transplantation. Typically, the transplantation is by injection into the cerebral ventricles.

Therapeutic use of PC can be applied to degenerative, demyelinating, excitotoxic, neuropathic and traumatic conditions of the CNS. Examples of conditions that can be treated via PC grafts include, but are not limited to, Parkinson's disease (PD), Huntington's disease (HD), Alzheimer's disease (AD), multiple sclerosis (MS), amyotrophic lateral sclerosis (ALS), epilepsy, stroke, ischemia and other CNS trauma.

Methods for transplanting various neural tissues into host brains have been described in Neural Transplantation: A Practical Approach, S. B. Dunnett & A. Bjorklund (Eds.) Irl Pr; 1992, incorporated by reference herein. These procedures include intraparenchymal transplantation, i.e. within the host brain (as compared to outside the brain or extraparenchymal transplantation), achieved by injection or deposition of tissue within the host brain so as to be opposed to the brain parenchyma at the time of transplantation.

The procedure for intraparenchymal transplantation involves injecting the donor cells within the host brain parenchyma stereotactically. This is of importance if it is required that the graft become an integral part of the host brain and to survive for the life of the host. In some embodiments, intraparenchymal transplantation involves pre-differentiation of the cells. Differentiation of the cells, however, limits their ability to migrate and form connections. Intraparenchymal transplantation of pre-differentiated cells is typically preferred when the objective is to achieve neurochemical production at the site of implantation. It has been observed, however, that undifferentiated PC can, upon implantation into the brain, differentiate as appropriate to the environment.

Alternatively, the graft may be placed in a cerebral ventricle or subdurally, i.e. on the surface of the host brain where it is separated from the host brain parenchyma by the intervening pia mater or arachnoid and pia mater. For subdural grafting, the cells may be injected around the surface of the brain. In some embodiments, the PC are injected intravenously. PC introduced intraventricularly or intravenously will migrate to the appropriate region on the host brain. Intraventricular (or intravenous) transplantation is preferred when the objective is restoration of circuitry and function.

Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. For grafting, the cell suspension is drawn up into the syringe and administered to anesthetized graft recipients. Multiple injections may be made using this procedure. Examples of CNS sites into which the PC may be introduced include the putamen, nucleus basalis, hippocampus cortex, striatum or caudate regions of the brain, as well as the spinal cord and ventricles.

The cellular suspension procedure permits grafting of PC to any predetermined site in the brain or spinal cord, is relatively non-traumatic, allows multiple grafting simultaneously in several different sites or the same site using the same cell suspension, and permits mixtures of cells having different characteristics. Multiple grafts may consist of a mixture of cell types. Alternatively, the graft consists of a substantially pure population of PC. Typically, from approximately $10^4$ to approximately $10^8$ cells are introduced per graft. The amount of cells used is typically constrained by volume, both in terms of a suitable volume for injection and constraints of the site into which the cells are to be injected. An implantation of 500,000 cells has been found to achieve suitable results, even where far fewer cells were needed. Any excess cells are cleared from the site, and no evidence has been found of implanted cells that failed to either migrate to a site of disease or damage or be cleared. Optionally, the PC can be grafted as clusters of undifferentiated cells. Alternatively, the PC can be induced to differentiate prior to implantation.

For transplantation into cavities, which may be preferred for spinal cord grafting, tissue is removed from regions close to the external surface of the CNS to form a transplantation cavity, for example by removing glial scar overlying the spinal cord and stopping bleeding with a material such a gelfoam. Suction may be used to create the cavity. The cell suspension is then placed in the cavity.

Grafting of PC into a traumatized brain will require different procedures. For example, the site of injury should be cleaned and bleeding stopped before attempting to graft. In addition, the donor cells should possess sufficient growth potential to fill any lesion or cavity in the host brain to prevent isolation of the graft in the pathological environment of the traumatized brain.

Genetically Modified PC

Although one advantage of the PC of the invention is the ability to use them without pre-differentiation or genetic modification, these cells are amenable to genetic modification. In some embodiments, the present invention provides methods for genetically modifying PC for grafting into a target tissue site or for use in screening assays and the creation of animal models for the study of disease conditions.

In one embodiment, the cells are grafted into the CNS to treat defective, diseased and/or injured cells of the CNS. The methods of the invention also contemplate the use of grafting of transgenic PC in combination with other therapeutic procedures to treat disease or trauma in the CNS or other target tissue. Thus, genetically modified PC of the invention may be co-grafted with other cells, both genetically modified and non-genetically modified cells, which exert beneficial effects on cells in the CNS. The genetically modified cells may thus serve to support the survival and function of the co-grafted, non-genetically modified cells.

Moreover, the genetically modified cells of the invention may be co-administered with therapeutic agents useful in treating defects, trauma or diseases of the CNS (or other target tissue), such as growth factors, e.g. nerve growth factor (NGF), gangliosides, antibiotics, neurotransmitters, neuropeptides, toxins, neurite promoting molecules, and antimetabolites and precursors of these molecules, such as the precursor of dopamine, L-dopa.

Vectors carrying functional gene inserts (transgenes) can be used to modify PC to produce molecules that are capable of directly or indirectly affecting cells in the CNS to repair damage sustained by the cells from defects, disease or trauma. In one embodiment, for treating defects, disease or damage of cells in the CNS, PC are modified by introduction of a retroviral vector containing a transgene or transgenes, for example a gene encoding nerve growth factor (NGF) protein. The genetically modified PC are grafted into the central nervous system, for example the brain, to treat defects, disease such as Alzheimer's or Parkinson's, or injury from physical trauma, by restoration or recovery of function in the injured neurons as a result of production of the expressed transgene product(s) from the genetically modified PC. The PC may also be used to introduce a transgene product or products into the CNS that enhance the production of endogenous molecules that have ameliorative effects in vivo.

Those skilled in the art will appreciate a variety of vectors, both viral and non-viral, that can be used to introduce the transgene into the PC. Transgene delivery can be accomplished via well-known techniques, including direct DNA transfection, such as by electroporation, lipofection, calcium phosphate transfection, and DEAE-dextran. Viral delivery systems include, for example, retroviral vectors, lentiviral vectors, adenovirus and adeno-associated virus.

The nucleic acid of the transgene can be prepared by recombinant methods or synthesized using conventional techniques. The transgene may include one or more fulllength genes or portions of genes. The polypeptides encoded by transgenes for use in the invention include, but are not limited to, growth factors, growth factor receptors, neurotransmitters, neuropeptides, enzymes, gangliosides, antibiotics, toxins, neurite promoting molecules, anti-metabolites and precursors of these molecules. In particular, transgenes for insertion into NPC include, but are not limited to, tyrosine hydroxylase, tryptophan hydroxylase, ChAT, serotonin, GABA-decarboxylase, Dopa decarboxylase (AADC), enkephalin, amphiregulin, EGF, TGF ($\alpha$ or $\beta$), NGF, PDGF, IGF, ciliary neuronal trophic factor (CNTF), brain derived neurotrophic factor (BDNF), neurotrophin (NT)-3, NT-4, and basic fibroblast growth factor (bFGF).

Although those skilled in the art appreciate the advantages of using genetically modified PC, it is also appreciated that, in some embodiments, it is preferable to use a preparation of PC that is free of genetically modified cells. As described in the Examples below, transplanted PC of the invention, free of genetically modified cells or other cell types, are able to migrate to a site of damage or dysfunction and adopt a phenotype tailored to the needs of the damaged region. This has been observed in both an animal model of Parkinson's disease and an animal model of epilepsy. Accordingly, the desired therapeutic effect can be achieved without any concerns that might be associated with use of transgenes and genetically modified cells.

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals. In one embodiment, the mammals are equine, canine, feline, porcine, ovine or rodent. In another embodiment, the subjects are rodent and human. The subject is typically a human.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to alleviate, reduce, cure or at least partially arrest symptoms and/or complications from the disease or condition. An amount adequate to accomplish this is defined as a "therapeutically effective dose."

Routes and frequency of administration of the therapeutic compositions disclosed herein, as well as dosage, will vary from individual to individual, and may be readily established using standard techniques. Typically, the pharmaceutical compositions are administered by injection. A single injection may suffice or, in some embodiments, between 1 and 10 doses may be administered over a 52 week period. Alternate protocols may be appropriate for individual patients.

A suitable dose is an amount of a substance that, when administered as described above, is capable of promoting a therapeutic response, and is at least a 10-50% improvement relative to the untreated level. In general, an appropriate dosage and treatment regimen provides the material in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

Pharmaceutical Compositions

The invention provides pharmaceutical compositions comprising PC and, optionally, a physiologically acceptable carrier. Pharmaceutical compositions within the scope of the present invention may also contain other compounds that may be biologically active or inactive. For example, one or more biological response modifiers may be present, either incorporated into a fusion polypeptide or as a separate compound, within the composition.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, intracranial, intraventricular or subdural administration. Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives.

EXAMPLES

The following examples are presented to illustrate the present invention and to assist one of ordinary skill in making and using the same. The examples are not intended in any way to otherwise limit the scope of the invention.

Example 1

Preparation of Progenitor Cells

This example demonstrates the preparation of brain progenitor cells (BPC), also referred to as neural progenitor cells (NPC). These same preparations, initially characterized as NPC (or BPC), were later determined to have features and express markers associated with pluripotent cells. The BPC were derived from the telencephalon (T lines) and mesencephalon (M lines) of fetal brain. Fetal tissue was obtained from physicians in the local area using the guidelines recommended by the National Institutes of Health. The donor was approached with the request for tissue donation only after an elective abortion was performed, and informed consent was subsequently obtained. No monetary compensation or other incentive were offered to the patient, gynecologist, or clinic. A sample of maternal blood was obtained and the following serologic tests were performed: HIV, hepatitis A, B, and C, HTLV-1, VDRL, and CMV. Fetal brain tissue was obtained through a low-pressure aspiration technique under sterile conditions. There was no change in the indication, timing, or methodology of the abortion between procedures. Fetal tissue immediately adjacent to the mesencephalon was cultured for aerobic and anaerobic bacteria, HSV, and CMV. Microscopic diagnosis was also performed using Gram stain. Fetal tissue from donors with a history of genital herpes, cancer, asthma, lupus, rheumatoid arthritis, allergies, vasculitis of autoimmune origin, drug abuse, or prostitution was excluded.

Gestation of the fetal cadaver was determined according to crown-to-rump length (CRL) as measured by ultrasound. The gestational age ranged from 6 to 8 weeks (CRL 20 to 24 mm). The samples of telencephalon and mesencephalon were obtained from 2 donors (CRL: 20 and 24 mm). Dissections were carried out at 4° C. in a laminar flow hood (Environmental Air Control, Inc.), under a dissecting microscope (Leica, Wild MJZ, Meerbrugg, Switzerland). A general purpose serum-free medium (Ultraculture, Whittaker Bioproducts) was used, with the addition of, 5 mMol of L-glutamine and 10 µg/ml of Kanamycin and 0.25 µg/ml of Fungizone. The fetal tissue was rinsed ten times with the culture medium, and then the brain was stripped of cartilaginous skull and the meninges and transferred to Hank's Balanced Salt Solution (HBSS) supplemented with 10 µg/ml of Kanamycin sulfate and 0.25 µg/ml of Fungizone for microdissection. The dorsal cortex from both hemispheres (telencephalon) was removed parasagittally. Further, the rostral half of ventral mesencephalon and tectum was dissected. Collected samples were thoroughly minced with microscissors and triturated using sterile fire-polished pipettes. No prior trypsinization was used. Before plating cells to culture flasks or onto glass chambered slides, the cell viability (Trypan Blue exclusion test) and density were assessed. Average viability was 96%. The optimal plating density was found to be 30,000 to 50,000 cells/$cm^2$.

Example 2

Characterization of Source Tissue

This example describes the characterization of tissue dissected for the above preparation of BPC. Areas of the fetal brain tissue adjacent to the dissected tissue were treated similarly and fixed for immunocytochemistry and electron- and light microscopy. These adjacent sections were analyzed retrospectively for viability and functional specificity.

For morphological analysis, cortex and mesencephalon were taken from the fetus and processed for immunocytochemistry or ultrastructural morphology. Following dissection, part of the tissue was fixed in 4% buffered (pH 7.4) PFA fixative, then embedded in paraffin and sectioned on a rotary microtome. Samples of this tissue were processed in a histochemical procedure to visualize the various neuronal and glial markers (AchE, TH, NSE, MAP2, BrDU, Nestin, etc.).

Immunocytochemical labeling with peroxidase reaction was carried out with antibodies to the glial marker glial fibrillary acidic protein (GFAP; Lipshaw, Philadelphia, Pa.), the neurotransmitter GABA (Sigma Chemical Co., St. Louis, Mo.), and a dopaminergic marker, the catecholaminergic synthesis enzyme TH (Sigma Chemical Co., St. Louis, Mo.). Briefly, sections were deparaffinized and rehydrated in a descending series of ethanol baths, then incubated in 3% hydrogen peroxide blocking solution (Signet Laboratories, Dedham, Mass.). The primary antibody was applied onto the slides, and then removed with two rinses of phosphate-buffered saline. Slides were then incubated in linking reagent and then labeling reagent, then visualized with AEC chromogen (Signet Laboratories, Dedham, Mass.). For electron microscopy, the tissue was fixed in Karnovsky's fixative, postfixed in 1% osmium tetroxide, dehydrated through a series of ethanols and propylene oxide, then embedded in Medcast resin (Ted Pella, Redding, Calif.). Ultrathin sections were collected on copper grids, stained with lead and uranium and viewed with a JEOL-100CX electron microscope.

After two to four passages, most of the cultured cells were harvested and frozen in liquid Nitrogen. Cryo medium contains the expansion culture medium with 10% DMSO, 4% of B-27 supplement, and 5 to 7 µl/ml of MEM non-essential amino acids solution (Gibco, N.Y.).

Cells were prepared for immunocytochemical staining using conventional techniques as described in U.S. patent publication number 20050118561, filed Dec. 2, 2004, and published Jun. 2, 2005. Cells were stained for glial fibrillary acidic protein (GFAP), neuron specific enolase (NSE), 5-Bromodeoxyuridine (BrDU), CD 34, and Leukocyte Common Antigen (CD 45). This staining protocol was also used with antibodies to Oct-4 (Chemicon), beta tubulin class III (Serotec), nestin (R&D Systems), tyrosine hydroxylase (Chemicon), and human mitochondria (Chemicon).

Example 3

Optimization of Culture Media

This example describes the various media components tested for their influence on expansion and differentiation of BPC. Growth rates of the telencephalon- and mesencephalon-derived BPC were compared in three standard culture media: Dulbecco's Modification of Eagle's Medium (DMEM); Eagle's Minimum Essential Medium (EMEM) without calcium (Biowhittaker), Neurobasal (GibcoBRL), Ultraculture (Biowhittaker), and PFMR-4+8F (BRF) with at least 25 variable combinations of mitogens bFGF, EGF, TGFα, LIF; Caspase 3 and 8 inhibitors; and B-27 supplement. The efficacy of each combination was tested by cell viability and doubling time during short- and long-term expansion, as well as behavioral effects in the rat PD model after intra-striatal transplantation. The EMEM-based, low calcium culture medium with addition of bFGF, EGF, TGFα, LIF, and B-27 presented with the best results.

After the numerous ingredients were tested, perhaps the most surprising result was the lack of benefit upon addition of the caspace-1 inhibitor, either acetyl-Tyr-Val-Ala-Asp (Ac-YVAD) or acetyl-Tyr-Val-Ala-Asp chloromethyl ketone (Ac-YVAD-CMK) (Calbiochem). In fact, the presence of caspace inhibitor in the growth medium was associated with decreased cell counts. In addition, no benefit was observed with the use of interleukin-1 (IL-1). Glial cell line-derived neurotrophic factor (GDNF) and ciliary neurotrophic factor (CTNF) were both found to prompt rapid differentiation and cell death.

Transforming growth factor alpha (TGFα) was found to shorten doubling time significantly (e.g., from 14 days to 5 days). Leukemia inhibitory factor (LIF) promoted neuronal cells and prevented the formation of large clusters of NPC. Basic fibroblast growth factor (bFGF) resulted in good proliferation, even when used in the absence of other trophic factors. Epidermal growth factor (EGF) alone did not support robust growth, but when combined with bFGF and TGFα, optimal growth was observed.

Cells grown in bFGF as the sole trophic factor were compared to NPC grown in medium containing EGF+BFGF+TGFα (E+F+T). Two million cells per animal were transplanted into PD rats (an animal model for Parkinson's disease). At 6 days post-transplant, the bFGF only cells showed a 12% decrease in density, while the E+F+T cells exhibited an increase in density of 167%.

Progenitor Expansion Medium
Basal Medium:
Eagle's Minimum Essential Medium (EMEM) without calcium, BioWhittaker, Inc., Walkersville, Md., cat #06-1746.
Supplements:
B27 (2%), Gibco BRL, cat#17504
r-hEGF (20 ng/ml), Peprotech, cat#100-15
r-hFGF basic (bFGF, FGF2), (20 ng/ml), Peprotech, cat#100-18B
Sodium Pyruvate (0.11 mg/ml), Sigma, cat#S-8636
Calcium Chloride $2H_2O$, (0.1 mM), Sigma, cat#C-7902
Optional:
Gentamicin (50 µg/ml), Sigma, cat#G-1272
Amphotericin B (1.25 µg/ml), Sigma, cat#A-2942
or Sigma's 100× antibiotic/antimycotic, cat#A-9909
Progenitor Differentiation Medium
Basal Medium:
PFMR-4+8F, Biological Research Faculty and Facility, Inc (BRFF), cat#SF-240
or DMEM, Neurobasal, or EMEM without calcium (brought up to 0.1 mM $CaCl_2$)
Differentiation Factors:
Glial Cell-Derived Neurotrophic Factor (GDNF) (10 ng/ml), Sigma, cat#G-1777
IL-1 alpha, (100 µg/ml), Sigma, cat#I-2778
IL-11 (1 ng/ml), Sigma, cat#I-3644
Leukemia Inhibitory Factor (LIF), (1 ng/ml), Sigma, cat#L-5283
$N^6$,2'-O-Dibutyryladenosine 3',5'-cyclic monophosphate (db-cAMP), (100 µM), Sigma, cat#D-0627
Forskolin (5 µM), Calbiochem-Behring Corp, cat#344270
Optional:
0.25 µg/ml fungizone
10 µg/ml kanamycin sulfate
Media Preparation:
Glutamate, when added to medium, is used only to provide for initial plating—subsequent feedings use medium without glutamate.

| Expansion Medium | | |
|---|---|---|
| Formulation | Recipe | Notes |
| 95.5 ml basal medium | 97.5 ml basal medium | Calcium-free EMEM preferred for progenitor cell expansion; for differentiation, can use EMEM, DMEM or Neurobasal |
| 0.05 mM $CaCl_2$ | 120 µl/100 ml | Only added to calcium-free EMEM; adjust quantity for expansion vs. differentiation |

-continued

Expansion Medium

| Formulation | Recipe | Notes |
|---|---|---|
| 2% B27 supplement | 2.0 ml B27 | |
| 0.5 mM L-glutamine | 0.25 ml 200 mM L-glutamine | Promotes growth of neurons (29.2 mg/ml) over glia, who prefer 2 mM L-glutamine 0.5 mM L-glutamine = 73 mg/L 100 ml med. = 7.3 mg = 0.25 ml 200 mM L-glutamine |
| 2 µg EGF (20 ng/ml) | 2 × 25 µl aliquot (40 ng/µl EGF) | |
| 1 µg FGF (10 ng/ml) | 1 × 25 µl aliquot (40 ng/µl FGF) | |
| 1 µg TGFα (10 ng/ml) | 1 × 25 µl aliquot (40 ng/µl TGFα) | |

Differentiation Medium

| Recipe | Formulation | Notes |
|---|---|---|
| 97.5 ml basal medium | 97.5 ml EMEM | BioWhitaker w/out calcium Cat#06-174G |
| 2.0 ml B27 | 2% B27 supplement | |
| 1 ml 11 mg/ml Na | 0.11 mg/ml sodium pyruvate | |
| 40 µl 25 mM CaCl$_2$ | 0.1 mM CaCl$_2$ | |
| 50 µl EGF(2 aliquots @40 ng/µl) | 2 µg EGF; 20 ng/ml EGF | |
| 50 µl bFGF(2 aliquots@40 ng/µl) | 2 µg FGF; 20 ng/ml FGF | |
| 25 µl TGFα(1 aliquot TGF@40 ng/µl) | 1 µg TGF; 10 ng/ml | |
| 100 µl LIF | 1 µg LIF; 10 ng/ml LIF | |

Neurobasal medium:

| Formulation | Recipe | Notes |
|---|---|---|
| 97.5 ml Neurobasal medium | 97.5 ml Neurobasal medium | |
| 2% B27 supplement | 2.0 ml B27 | |
| 0.5 mM L-glutamine | 0.25 ml 200 mM L-glutamine | Promotes growth (29.2 mg/ml) of neurons over glia, who prefer 2 mM L-glutamine |
| 25 µM L-Glutamic acid | 184 µl 2 mg/ml L-glutamic acid (20 mg L-Glu + 10 ml ddH$_2$0) | Helps cells attach |
| 2 µg EGF (20 ng/ml) | 2 × 25 µl aliquot @40 ng/µl | |
| 1 µg FGF (10 ng/ml) | 1 × 25 µl aliquot @40 ng/µl | |
| 1 µg TGFα (10 ng/ml) | 1 × 25 µl aliquot @40 ng/µl | |

Once made, this medium keeps 1-2 weeks refrigerated.

Example 4

Features of Cells Cultured in Media of the Invention

The PC cultured in the medium of the invention have been shown to have the characteristics of neural progenitor cells: they can be maintained indefinitely in EMEM culture, show positive staining for BrDU, express Nestin, under low [Ca++] conditions they are capable of generating dopaminergic (35-60%) and serotonergic (24-40%) neurons as well as a number of other MAP2 positive cells (10-12%), and glia (GFAP positive cells 15-23%). They also sporadically generate nucleated red cells (2-3%) in vitro and myoblasts when injected into the ischemic rat heart.

In contrast, PC will remain in suspension and undifferentiated when cultured in the low calcium medium EMEM of the invention. As the calcium concentration is raised, e.g., to 0.1 mM, then the PC form networks and exhibit a neuronal phenotype. Even without the addition of LIF to favor neurons over glia, only 1-2% of these cultured cells are immunopositive for the glial marker GFAP, suggesting that the population is primarily neuronal.

Example 5

Transplantation of PC into Brain in an Animal Model of Parkinson's Disease

This example demonstrates that PC prepared in accordance with the invention can be successfully grafted into rat brain. The example shows that grafted cells can exhibit normal differentiation into tyrosine hydroxylase (TH) positive cells. In addition, the results show that the grafted PC ameliorate the behavioral deficit characteristic of this animal model of Parkinson's disease.

For implantation, free-floating PC are removed from the culture flask and spun as is done for medium changes. The pellet is re-suspended in the remaining 2 mls of medium, and this concentrated suspension is counted on a hemacytometer. Additional medium is added to bring the final cell concentration to 350,000 cells/µl.

The substantia nigra was lesioned via injection of 4 µl (8 µg) 6-hydroxydopamine, 6-OHDA (Research Biomedicals International, Mass.) using a Hamilton syringe (Hamilton Co., Nev.). The injection was carried out over 2 minutes, with a three minute wait after injection to allow diffusion before removal of the needle.

Two weeks following nigral lesion, rats were placed under general anesthesia (Ketamine 87 mg/kg and Xylazine 10 mg/kg; or 4% isoflurane gas) and fixed in a stereotaxic apparatus. The scalp incision was made and a hole was drilled in the skull at the coordinates of the striatum. The progenitor cells were implanted using a Hamilton syringe (70,000 cells/2 µl per animal) into the striatum ipsilateral to the 6-OHDA lesion, at stereotaxic coordinates A=−0.11; L=3.8; V=4.5. The incision was then closed and treated with Betadine. All PCs were implanted without prior conditioning.

For rotational behavior testing, rats were injected subcutaneously with amphetamine or vehicle. Immediately after injection, animals were placed in a locomotor chamber measuring 3 feet by 3 feet (Columbus Instruments, Columbus, Ohio). Following a two-minute adjustment period, all rotations were tracked by a CCD camera mounted over the chamber and analyzed by the Videomex V™ video image analyzer (Columbus Instruments, Columbus, Ohio). Locomotor activity and rotation were recorded for 60 minutes.

Both groups of animals that received T5 or M5 cells showed significant and comparable reduction in their rotational behavior. In both groups of animals, about 14-24% of the PCs differentiated into TH-positive cells.

Example 6

Cells Implanted in Substantia Nigra Become Tyrosine Hydroxylase Positive

PC, both M5 and T5 cells, were implanted using a method similar to that described in Example 5 above. The M5 cell population, derived from brainstem, was 24-30% positive for tyrosine hydroxylase (TH) prior to implantation. After implantation, 54% of the M5 NPC were TH positive. The T5 cells, derived from forebrain, were all TH negative in culture. Once implanted, 32% of the implanted PC were TH positive.

Example 7

Differentiation of PC

Culture conditions as described above were varied and manipulated to determine the optimal conditions to induce differentiation of PC. The resulting optimized differentiation medium contains 0.15 mM Ca++, 0.5 mM L-glutamine, 10 ng/ml GDNF, 15 ng/ml retinoic acid.

Example 8

Cryopreservation of PC

Media ingredients were varied and manipulated to determine the optimal conditions for cryopreservation of PC. B27, in addition to DMSO, appears to provide a significant protective effect contributing to the exceptionally high viability observed in thawed PC.

For cryopreservation, PC were suspended in a low calcium medium (0.06 mM Ca++ EMEM) supplemented with 2% B27, LIF (15 ng/ml), EGF (50 ng/ml), FGF and TGF (25 ng/ml) and 10% DMSO. The cells are first placed in a freezer at about −40° C. for 1 to 1.5 hours, after which they are stored in liquid nitrogen. Cells can be stored at below about −80° C., typically at about −200° C. The liquid nitrogen storage tank used in these studies is maintained at −197° C.

For thawing, both the culture medium and the flask was pre-warmed to 37° C. in a water bath at 37° C. Using this cryopreservation method, over 95% viability is consistently observed in the PC upon thawing (using dye exclusion cell counts). Typically, the cells appear shrunken and of abnormal morphology for the first 5-7 days after thawing. Despite this appearance, the cells are able to exclude trypan blue dye. After about one week, the cells recover to their pre-freezing state, exhibiting typical morphology, growth and doubling times.

Example 9

Pluripotent Cells in Cultures of the Invention

Cells cultured as described above for NPC have been evaluated for expression of the stem cell marker Oct-4. Oct-4 ("octamer-4") is a transcription factor that is specifically expressed in embryonic and adult stem cells and tumor cells, but not in cells of differentiated tissues (Tai et al., Carcinogenesis, published online Oct. 28, 2004). Oct-4-positive cells are also capable of developing in culture into oogonia that enter meiosis, recruit adjacent cells to form follicle-like structures, and later develop into blastocysts (Hubner, K. et al., Science, 2003, 300(5623):1251-6). This capacity for oogenesis in culture makes them useful for nuclear transfer and manipulation of the germ line, and as well as to create models for studies on fertility treatment and germ and somatic cell interaction and differentiation.

Cells cultured as described above for NPC, by six weeks in culture, will show some stem cells (Oct-4-positive), and mostly nestin-positive progenitor cells. Over a period of four months in culture, the population shifted from containing about 5% Oct-4-positive cells to about 30% Oct-4-positive cells. This observation could indicate that these cells de-differentiate in long-term culture. Alternatively, this may reflect a selective survival of stem cells in long-term culture.

Figure 17:
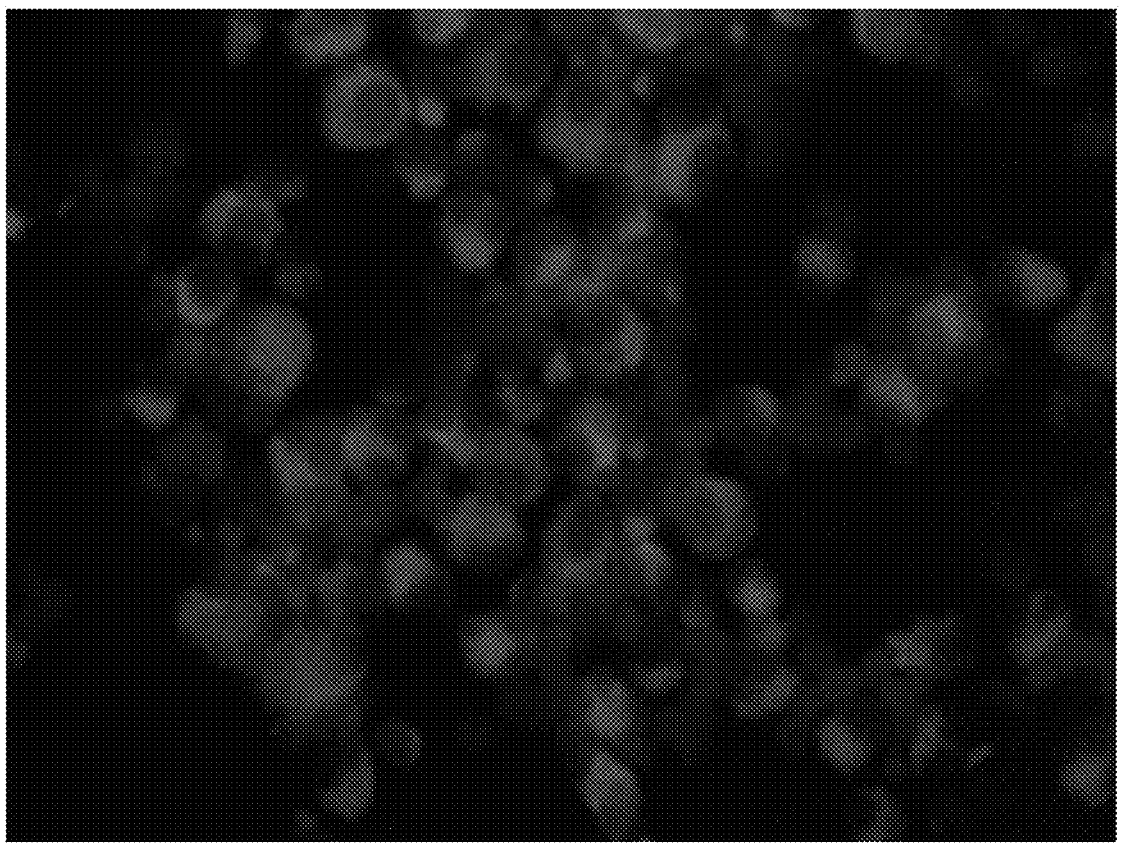
FIG. 17 is a photomicrograph showing co-expression of nestin and Oct-4 in the same NPCs, green fluorescence representing Oct-4 and red representing nestin. 20×.

Oct-4-positive cells were also observed to co-express the NPC marker, nestin, as shown in FIG. 17. Nestin-positive cells are thus capable of differentiating into neural cells, but not necessarily committed to this path.

Example 10

Implanted PCs Restore Function in Animal Model of Parkinson's Disease

Nigral lesions were performed in rats as described above in Example 5 to create the rotational behavior deficit characteristic of this rat model of Parkinson's disease. 500,000 human NPC prepared as described above were injected into the cerebral ventricle. After completion of rotational behavior studies, which confirmed successful amelioration of rotational behavior, tissues sections were prepared for immunohistochemical examination. Human cells from the implanted PCs were found to have migrated to neural structures including the striatum, substantia nigra and hippocampus, and to differentiate into neurons and glia.

Figure 18:
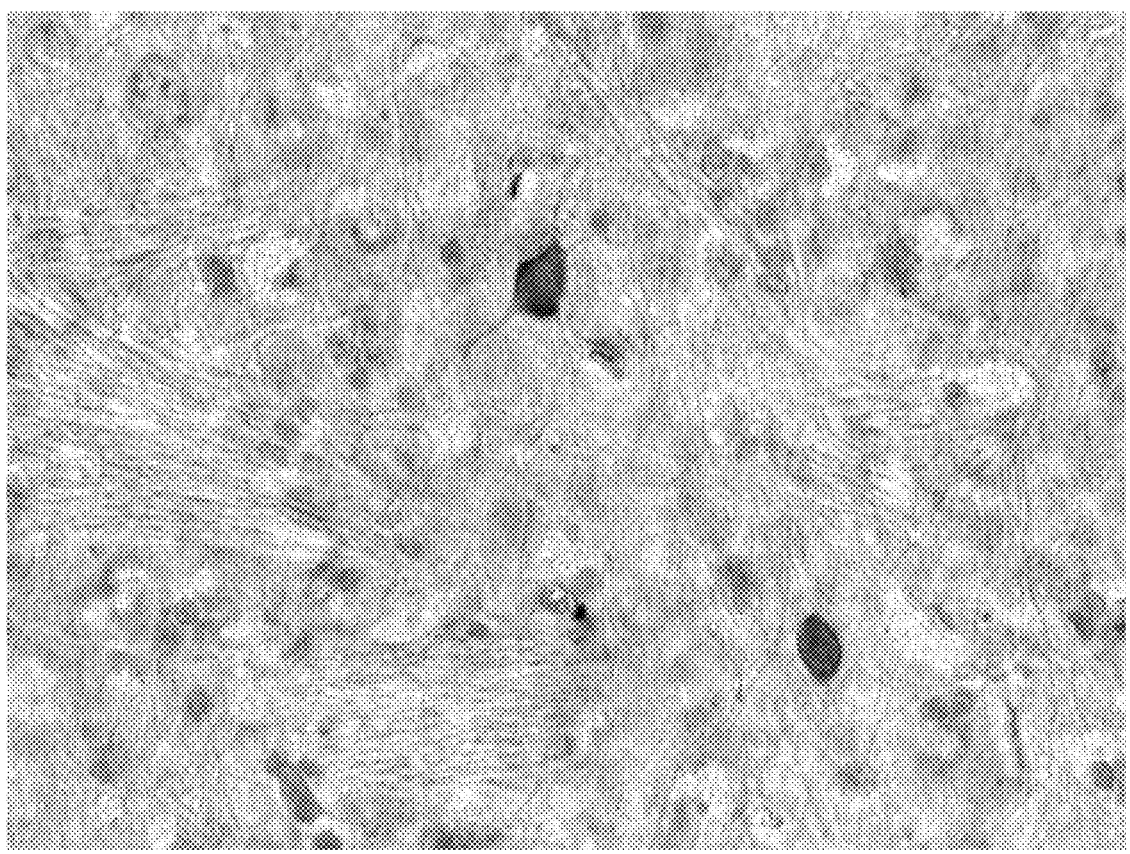
FIG. 18 is a photomicrograph showing an amber-brown human neuron with the branching extensions at the center of the picture and a glial cell at the right lower corner of the picture in the rat putamen. These cells migrated from the cerebral ventricle of the animal that showed a 70% improvement in its rotational behavior 4 months after the intraventricular injection of 500,000 undifferentiated brain progenitor cells. Anti-human mitochondrial antibodies. 40×
Figure 19:
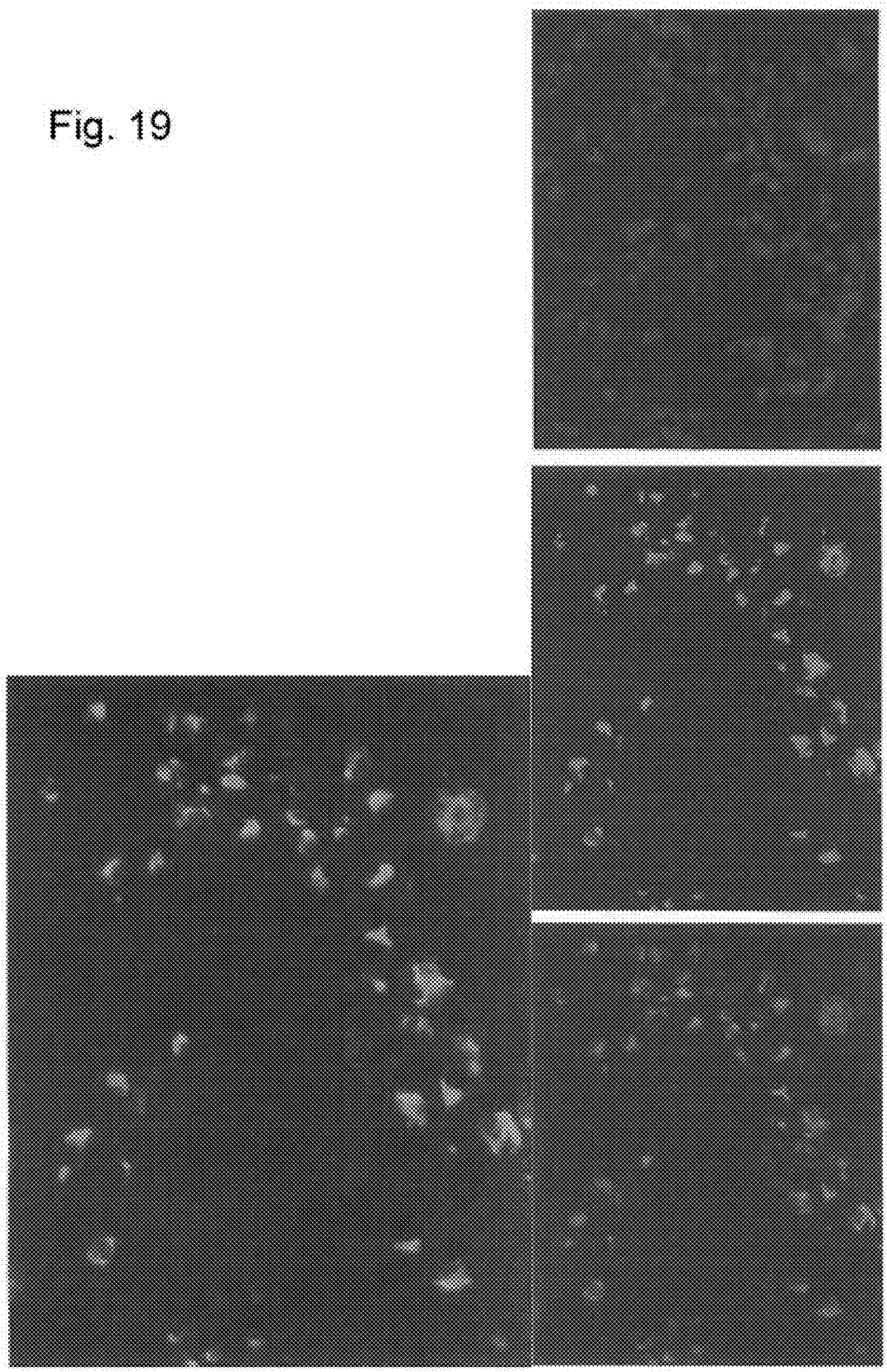
FIG. 19 is a series of photomicrographs showing doublestaining of PC for nestin (center panel; Texas red) and TRA-1-60 (right panel; FITC). Nuclei are stained with DAPI (left panel) to reference cell location, size and shape. The lower panel shows all 3 images overlaid, indicating that most cells express characteristics of both embryonic, undifferentiated cells (TRA-1-60) and partially differentiated neural progenitor cells (nestin) simultaneously. 40×
Figure 20:
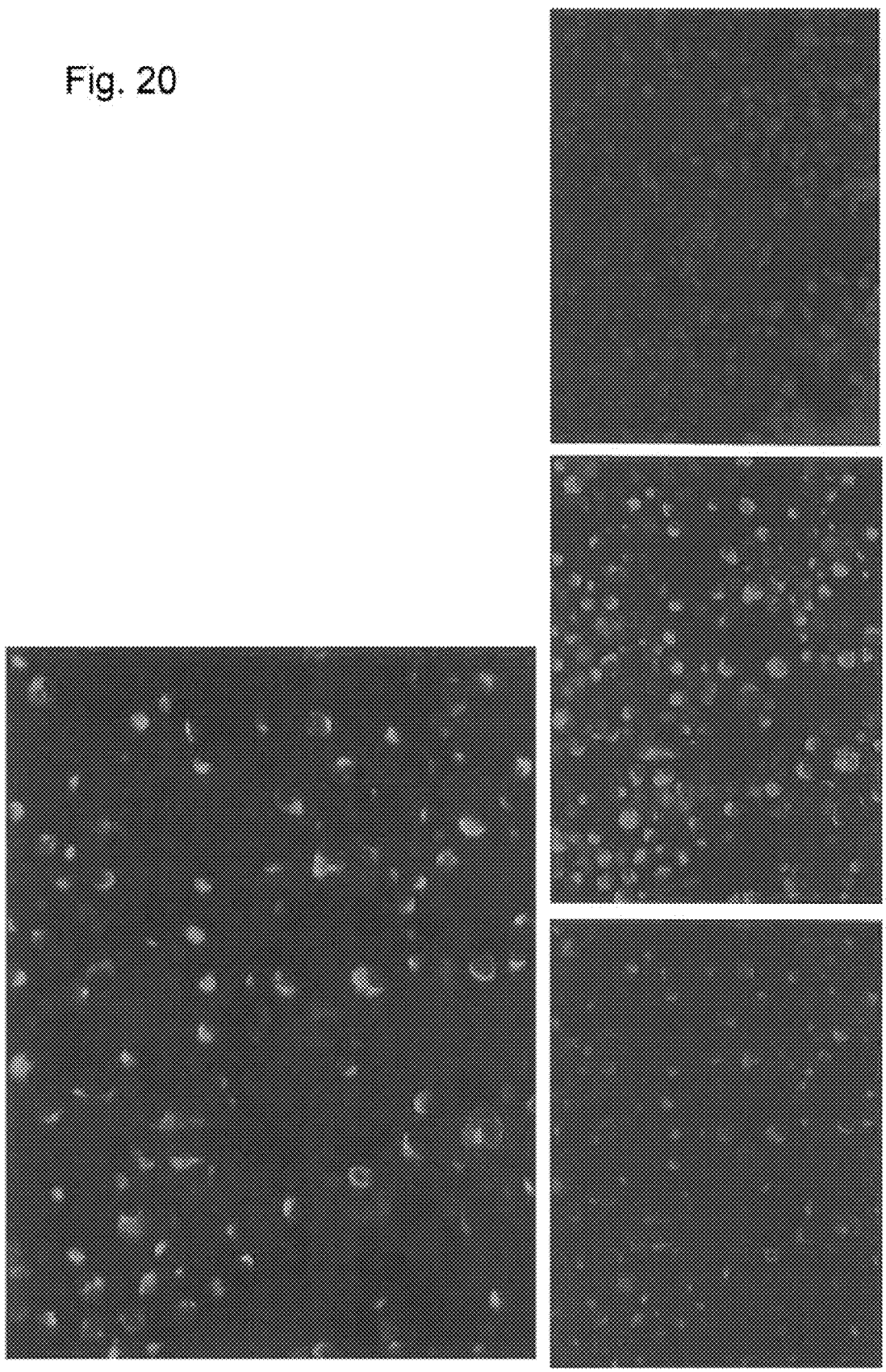
FIG. 20 is a series of photomicrographs showing doublestaining of PC for nestin (center panel; Texas red) and TRA-1-81 (right panel; FITC). Nuclei are stained with DAPI (left panel) to reference cell location, size and shape. The lower panel shows all 3 images overlaid, indicating that most cells express characteristics of both embryonic, undifferentiated cells (TRA-1-81) and partially differentiated neural progenitor cells (nestin) simultaneously. 40×
Figure 21:
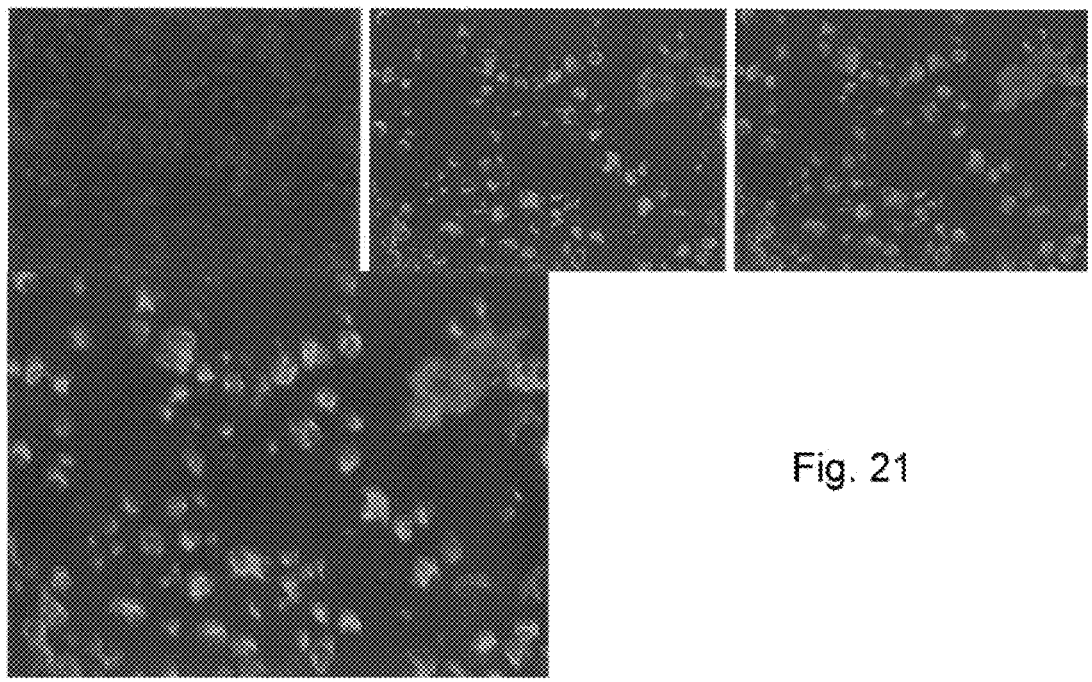
FIG. 21 is a series of photomicrographs as in FIGS. 19 and 20, except with SSEA-4 as the marker for embryonic stem cells (right panel, FITC). 40×
Figure 22:
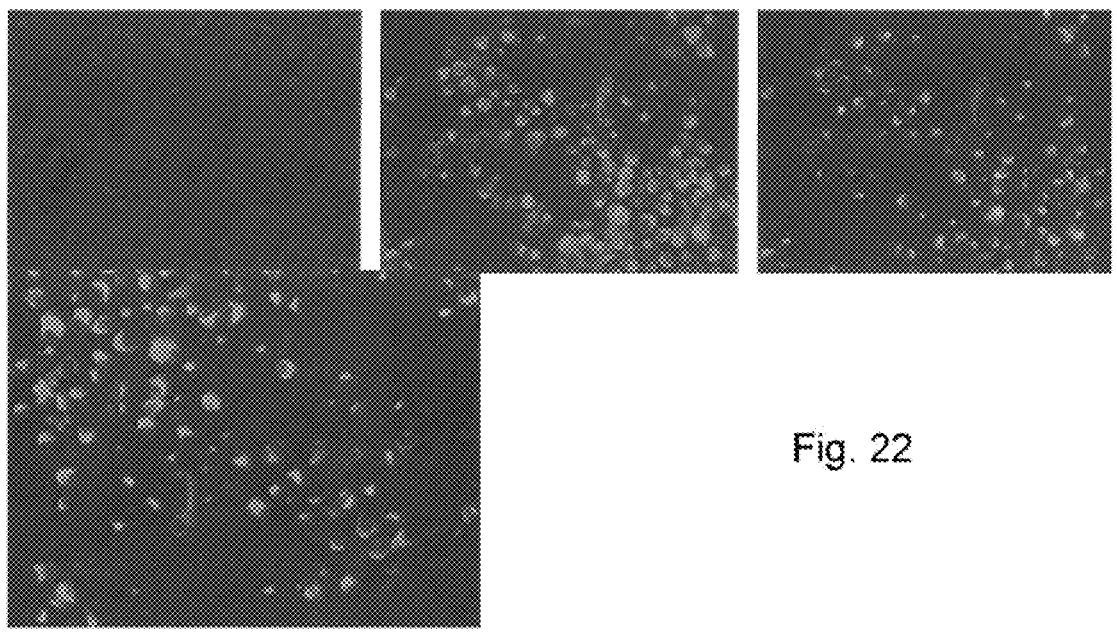
FIG. 22 is a series of photomicrographs as in FIGS. 19-21, except with SSEA-1 as the marker, which is associated with partially differentiated cells (right panel, FITC). 40×

FIG. 18 is a photomicrograph showing an amber-brown human neuron with the branching extensions at the center of the picture and a glial cell at the right lower corner of the picture in the rat putamen. These cells migrated from the cerebral ventricle of the animal that showed a 70% improvement in its rotational behavior 4 months after the intraventricular injection of 500,000 undifferentiated neural progenitor cells. Anti-human mitochondrial antibodies. 40×.

Example 11

Co-Expression of Markers for NPC and Pluripotent Cells

This example demonstrates that cells derived from human fetal forebrain and propagated in vitro as described in the preceding examples express features of both neural progenitor cells and pluripotent cells. The cells were immunostained with antibodies directed against nestin, a marker for partially differentiated neural progenitor cells, and with a second antibody directed against a marker for pluripotent embryonic stem cells. Four different markers were tested: TRA-1-60, TRA-1-81, SSEA-4 (pluripotent cell markers) and SSEA-1 (progenitor cell marker). All four were found co-expressed in the same cells with nestin. Representative images showing double-stained cells are presented in FIGS. 19-22. The nuclear stain DAPI was used to reference cell location, size and shape.

The cell populations of the invention have been cultured for over three years, and the proportion of various markers expressed in these populations have been found to shift toward markers associated with undifferentiated cells over time. The percentage of cells expressing these markers as of year 1, year 2 and year 3 in culture is shown in the following table.

| Cell Marker | Year 1 | Year 2 | Year 3 |
| --- | --- | --- | --- |
| Neuron Specific Enolase (NSE) | 32% | 15% | 7% |
| Tyrosine Hydroxylase (TH) | 29% | 7% | 2% |
| Glial Fibrillary Acidic Protein (GFAP) | 55% | 1% | 1% |
| GABA | 2% | 3% | 2% |
| Nestin | 68% | 99% | 99% |
| Oct-4 | 16% | 64% | 98% |
| Human Mitochondria | 100% | 100% | 100% |
| Telomerase (hTERT) | | | 98% |
| p53 | | | 58% |

Example 12

Pluripotent Cells Transplanted to Ventricle Migrate to Damaged Hippocampus

This example demonstrates the damage-specific migration of transplanted pluripotent cells. Kainic acid was injected unilaterally into rat hippocampus in accordance with conventional protocol for this animal model of epilepsy. The contralateral hippocampus served as an intra-subject control. Pluripotent cells of the invention (500,000 or 1,000,000 cells per subject) were injected into the ventricle. After 10 days, hippocampal tissue sections were obtained and stained using anti-human nestin. As illustrated in FIG. 23, the transplanted cells were found to migrate to the damaged hippocampus and not to the contralateral healthy hippocampus.

Procedure 1: Excitotoxic Lesion of the Dopaminergic Neurons.

Under general anesthesia (Ketamine 87 mg/kg and Xylazine 10 mg/kg or Isofluorane gas at 4% for induction and 1.5% for maintenance), female Sprague-Dawley rats were placed into a stereotaxic apparatus. The heads of the subjects were shaved using an electric razor, and the area to be incised was cleaned with betadine. An incision was made in the scalp, a hole was drilled in the skull, and the rat received a stereotactic injection of 6-OHDA into the substantia nigra. Stereotaxic coordinates from bregma midline and dura with incisor bar +3.3: A=5.0, L=2.0, V=8.0. The incision was then closed with staples and treated with Betadine; instruments were sterilized with alcohol between each use. Rats were given 1 cc of subcutaneous sterile saline, placed on a heating pad and monitored closely until they woke up. Rats were monitored daily for one week post-op during their recovery, and given additional injections of subcutaneous saline if dehydration was observed.

Procedure 2: Kainic Acid Injection

Adult male (150-250 gm) Sprague Dawley rats were anesthetized using Ketamine 87 mg/kg and Xylazine 10 mg/kg or Isofluorane gas at 4% for induction and 1.5% for maintenance), and unilaterally injected with kainic acid (KA) (0.4 µg/0.2 µl normal saline) in the right posterior hippocampus [anteroposterior (AP), −5.6 mm; mediolateral (ML) 4.0 mm; dorsoventral (DV) 7.0 mm. Beginning 2-3 months after injection, rats were observed during repeated 16-24 hr video monitoring periods for 1-2 weeks to detect spontaneous behavioral seizures.

Procedure 3: Grafting Cells to the Striatum, Hippocampus, or Lateral Ventricles of Adult Rats Two to three weeks following nigral and hippocampal lesion (above), rats were again placed under general anesthesia (see procedure 1 and 2) and fixed in a stereotaxic apparatus. The scalp incision was re-opened and a second hole drilled in the skull at the coordinates of the striatum. The pluripotent cells were implanted into the striatum, hippocampus or brain ventricles ipsilateral to the 6OHDA lesion, at stereotaxic coordinates Anterior-Posterior (AP) −0.11; Medial-Lateral (ML) 3.8 mm; Vertical (V) −4.5 mm for the striatum; AP −5.6 mm; ML 4.0 mm; V 7.0 mm for the hippocampus AP −0.8 mm; ML −1.5 mm; V −4.5 mm, and for the lateral brain ventricle AP −1.0 mm, ML −1.8 mm, V −3.5 mm.

Example 13

Multi-Lineage Differentiation of Pluripotent Cells Transplanted into Hippocampus This example demonstrates that human pluripotent cells of the invention will repopulate the damaged CA3 zone of the hippocampus of kainic acid-treated rats, and that these transplanted cells will differentiate into neurons and astrocytes. FIGS. 24A, C and D show the transplanted cells at 10 days after injection. The presence of these human cells in the CA3 zone is shown in FIG. 24A using anti-human mitochondria staining. By 16 days after injection, transplanted cells have differentiated into GABAergic neurons, as shown in FIG. 24B. The presence of this inhibitory neurotransmitter indicates that the transplanted cells have differentiated into a phenotype that will counteract the excessive excitatory activity of the epileptogenic hippocampus.

The presence of both neurons (FIG. 24C) and astrocytes (FIG. 24D) indicates that the transplanted cells (identified by anti-human mitochondria staining) have differentiated into different cell populations by 10 days after transplantation. As shown in the insets of FIGS. 24A-D, the contralateral, intact side of the brain is free of the transplanted pluripotent cells.

Example 14

Implanted Cells Restore Structure of Lesioned Brain and End Seizure Activity This example demonstrates that human pluripotent cells of the invention will repopulate the brain after extensive damage induced by kainic acid lesions. In addition, lesion-induced seizure activity stopped in subjects receiving intraventricular injection of pluripotent cells.

Rats were lesioned with kainic acid as described in Example 13. This treatment obliterates approximately one third of the brain volume, creating a large cavity in the cerebrum, and leaves the subject experiencing massive and repeated seizure activity. In this study, of 48 subjects receiving these lesions, 24 received intraventricular injection of 500,000 pluripotent cells of the invention six months following the kainic acid lesion. The remaining 24 subjects received control treatment.

Seizure activity was recorded for 12 hours daily. Essentially, implantation of pluripotent cells into the ventricles of KA-lesioned rats resulted in a shift from a chronic disease condition to an acute condition. A further group of rats was then implanted with pluripotent cells concurrently with KA-lesion. In these subjects, no cerebral cavity was observed, and no seizure activity developed. In other words, pluripotent cells were able to prevent the massive kainic acid-induced cavity formation and seizures. This remarkable protective effect of pluripotent cells indicates that administration of the cells is most optimal if performed shortly after a seizure has occurred, thereby minimizing the cerebral damage caused by the seizure activity and hence reducing further seizure activity resulting from seizure-induced damage.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A composition comprising a plurality of isolated mammalian cells that co-express nestin and a marker of pluripotent cells, and a culture medium that has a total calcium concentration of 0.03 to 0.15 mM, wherein the cells are suspended in the culture medium and wherein the cells continue to proliferate in an undifferentiated state for at least 4 months.

2. The composition of claim 1, wherein the marker of pluripotent cells is selected from the group consisting of TRA-1-60, TRA-1-81 and SSEA-4.

3. The composition of claim 1, wherein the cells have a doubling rate of less than 12 days.

4. The composition of claim 1, wherein the cells have a doubling rate of about 5 days.

5. The composition of claim 1, wherein the cells continue to proliferate for 2 years in vitro.

6. The composition of claim 1, wherein the cells are obtained from fetal forebrain.

7. The composition of claim 1, wherein the medium has a total calcium concentration of less than 0.1 mM.

8. The composition of claim 7, wherein the total calcium concentration is about 0.05 mM.

9. The composition of claim 1, wherein the medium further comprises:
   (a) about 15-100 ng/µl epidermal growth factor (EGF);
   (b) about 10-150 ng/µl basic fibroblast growth factor (bFGF);
   (c) about 10-75 ng/µl transforming growth factor-alpha (TGFα).

10. The composition of claim 9, further comprising:
    (d) about 25-150 ng/µl leukemia inhibiting factor (LIF).

11. The composition of claim 10, wherein the LIF is about 25 ng/µl.

12. The composition of claim 9, wherein the EGF is about 20 ng/µl.

13. The composition of claim 9, wherein the bFGF is about 10 ng/µl.

14. The composition of claim 9, wherein the TGFα is about 10 ng/µl.

15. The composition of claim 9, wherein the culture medium is free of a feeder layer.

16. The composition of claim 9, wherein the culture medium is serum-free.

17. The composition of claim 9, further comprising 0.5-2.5% B27 supplement.

18. The composition of claim 9, wherein the growth factors EGF, bFGF and TGFα are recombinant growth factors.

19. The composition of claim 9, wherein the cells and the growth factors are human.

20. The composition of claim 9, wherein the culture medium further comprises about 0.11 mg/ml sodium pyruvate.

21. A method of propagating pluripotent cells, comprising culturing the composition of claim 1.

22. The method of claim 21, wherein the culturing is in the absence of a feeder layer.

23. A plurality of isolated mammalian cells that co-express nestin and a marker of pluripotent cells, wherein the cells are immunopositive for nestin and for a marker of pluripotent cells, the marker selected from the group consisting of TRA-1-60, TRA-1-81 and SSEA-4, and a culture medium, wherein the cells are suspended in the culture medium, wherein the culture medium has a total calcium concentration of 0.03 to 0.09 mM, and wherein the cells continue to proliferate in an undifferentiated state for at least 4 months.

* * * * *